United States Patent
Pellicci et al.

(10) Patent No.: US 7,915,304 B2
(45) Date of Patent: Mar. 29, 2011

(54) PHENYL SUBSTITUTED MALEIMIDES AS MEDICAMENTS FOR BLOCKING DEGENERATIVE TISSUE DAMAGES BY INHIBITING MPT

(75) Inventors: PierGiuseppe Pellicci, Opera (IT); Marco Giorgio, San Genesio (IT); Saverio Minucci, Noverasco Opera (IT); Paolo Bernardi, Padua (IT); Gilles Pain, Castelforte (IT); Stephen Martin Courtney, Abingdon (GB); Christopher John Yarnold, Abingdon (GB); Joachim Kraemer, Hamburg (DE)

(73) Assignee: Congenia S.r.l., Milan (IT)

( * ) Notice: Subject to any disclaimer, the term of this patent is extended or adjusted under 35 U.S.C. 154(b) by 0 days.

(21) Appl. No.: 12/444,407
(22) PCT Filed: Sep. 21, 2007
(86) PCT No.: PCT/EP2007/008238
§ 371 (c)(1), (2), (4) Date: Apr. 6, 2009
(87) PCT Pub. No.: WO2008/067863
PCT Pub. Date: Jun. 12, 2008

(65) Prior Publication Data
US 2010/0099736 A1  Apr. 22, 2010

(30) Foreign Application Priority Data
Oct. 24, 2006 (EP) .................................... 06022194

(51) Int. Cl.
*A01N 43/36* (2006.01)
*A61K 31/40* (2006.01)
(52) U.S. Cl. ....................... 514/425; 514/866
(58) Field of Classification Search ............... 514/425, 514/866
See application file for complete search history.

(56) References Cited

U.S. PATENT DOCUMENTS

2002/0127605 A1*  9/2002  Hamilton et al. .............. 435/7.1
2004/0248885 A1    12/2004 Auguet et al.
2007/0185174 A1    8/2007  Auguet et al.

FOREIGN PATENT DOCUMENTS
WO  03 009843  2/2003

OTHER PUBLICATIONS

Ferreira FM, Seiça R, Oliveira PJ, Coxito PM, Moreno AJ, Palmeira CM, and Santos MS, "Diabetes induces metabolic adaptations in rat liver mitochondria: role of coenzyme Q and cardiolipin contents," Biochimica et Biophysica Acta, Oct. 2003, 1639(2), 113-120.*

(Continued)

*Primary Examiner* — San-ming Hui
*Assistant Examiner* — Paul Zarek
(74) *Attorney, Agent, or Firm* — Oblon, Spivak, McClelland, Maier & Neustadt, L.L.P.

(57) ABSTRACT

The invention discloses the use of a compound of formula (I), wherein $R^1$, $R^2$, $R^3$, and $R^4$ each independently represents: hydrogen; halo; hydroxy; ($C_1$-$C_6$) alkyl optionally substituted by hydroxy or ($C_1$-$C_4$) alkoxy; ($C_1$-$C_6$) haloalkyl; ($C_1$-$C_6$) alkoxy; and ($C_1$-$C_6$) haloalkoxy; for the preparation of a medicament for the prevention and/or treatment of diseases resulting from opening of the MPTP which are characterized by degenerative tissue damages, in particular, diabetes and diabetic complications, neurological diseases and stroke, heart infarction, inherited dystrophies and hepatitis, more particularly, diabetic vascular diseases, such as diabetic retinopathy, and neurodegenerative disorders, such as multiple sclerosis. Further objects are a group of selected individual compounds of formula (I) for use as medicaments and a further group of selected individual compounds of formula (I) as novel compounds.

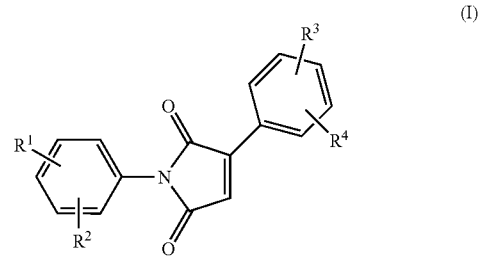

17 Claims, 1 Drawing Sheet

OTHER PUBLICATIONS

National Institute of Diabetes and Digestive and Kidney Diseases (NIDDK), "Diabetes Prevention Program," http://diabetes.niddk.nih.gov/dm/pubs/preventionprogram/, Oct. 2008.*

Landenranta J, Sidman RL, Pasqualini R, and Arap W, "Treatment of hypoxia-induced retinopathy with targeted proapoptotic peptidomimetic in a mouse model of disease," FASEB J, Oct. 2007, 21(12), 3272-3278 (Epub May 18, 2007).*

Mattson, M. et al., "Mitochondria in cell death: novel targets for neuroprotection and cardioprotection", Trends in Molecular Medicine, vol. 9, No. 5, pp. 196-205, XP002427639, (2003).

Kroemer, G. et al., "The Mitochondrial Permeability Transition Pore Complex as a Pharmacological Target. An Introduction", Current Medicinal Chemistry, vol. 10, No. 16, pp. 1469-1472, XP008077265, (2003).

Hirsch, T. et al., "Role of the Mitochondrial Permeability Transition Pore in Apoptosis", Bioscience Reports, vol. 17, No. 1, pp. 67-76, XP019274333, (1997).

Chernyak, B.V., "Redox Regulation of the Mitochondrial Permeability Transition Pore", Bioscience Reports, vol. 17, No. 3, pp. 293-302, XP019274342, (1997).

Morin, D. et al., "Effect of the mitochondrial transition pore inhibitor, S-15176, on rat liver mitochondria: ATP synthase modulation and mitochondrial uncoupling introduction", Biochemical Pharmacology, vol. 72, No. 7, pp. 911-918, XP005629834, (2006).

Hausenloy, D. et al., "Inhibiting mitochondrial permeability transition pore opening: a new paradigm for myocardial preconditioning?", Cardiovascular Research, vol. 55, No. 3, pp. 534-543, XP002381018, (2002).

Yuki, H. et al., "Studies on Antiviral Agents. II. Synthesis and biological Activity of Maleimide Derivatives", Chemical and Pharmaceutical Bulletin, vol. 15, No. 8, pp. 1101-1106, XP002985950, (1967).

* cited by examiner

PHENYL SUBSTITUTED MALEIMIDES AS MEDICAMENTS FOR BLOCKING DEGENERATIVE TISSUE DAMAGES BY INHIBITING MPT

CROSS REFERENCES TO RELATED APPLICATIONS

This application is a 371 of International Patent Application No. PCT/EP2007/008238, filed on Sept. 21, 2007, and claims priority to European Patent Application No. 06022194.2, filed on Oct. 24, 2006.

DESCRIPTION

The present invention relates to the use of compounds inhibiting the opening of the mitochondrial permeability transition pore (MPTP) in cells for the preparation of medicaments for the prevention and/or treatment of diseases resulting from opening of the MPTP which are characterized by degenerative tissue damages.

BIOLOGICAL BACKGROUND

The mitochondrial permeability transition (MPT) is a sudden increase of the inner membrane permeability to solutes with molecular mass below approximately 1500 Da with consequent mitochondrial swelling and release of cytochrome C. The key mitochondrial mechanism causing MPT is opening of the permeability transition pore (PTP), a high-conductance inner membrane channel whose entire molecular components are still to be fully identified (Forte, M.; Bernardi, P. Genetic dissection of the permeability transition pore. J. Bioenerg. Biomembr., 2005, 37, 121-8).

The PTP open state dissipates the proton electrochemical gradient resulting in $Ca^{2+}$ release and ATP hydrolysis and is a potential cause of osmotic swelling. This in turn can cause inner membrane unfolding and outer membrane rupture followed by release of proapoptotic intermembrane proteins into the cytosol. The PTP open-closed state is regulated by multiple effectors acting at various sites and many of these sites are affected by conditions and mediators implied in a variety of models of cell death (Bernardi, P. Mitochondrial transport of cations: Channels, exchangers and permeability transition. Physiol. Rev., 1999, 79, 1127-1155). Hence PTP opening is one mitochondria-mediated mechanism for promoting cell death.

Programmed cell death (apoptosis) is an essential process of multicellular organisms and the physiological rate of apoptosis controls normal development and tissue renewal. However, an increased rate of apoptosis is found in many pathological conditions characterized by excessive cell loss and tissue degeneration. A wide number of cellular stresses cause functional and structural changes to mitochondria that, through cell death, impinge on tissue homeostasis and functionality (Green, D. R.; Kroemer, G. The pathophysiology of mitochondrial cell death, Science, 2004, 305, 626-629). An increased rate of apoptosis in stem cell compartments affects tissue renewal and accelerates aging whilst a reduction of functioning cell mass impairs tissue performance directly (Pelicci, P. G. Do tumor-suppressive mechanisms contribute to organism aging by inducing stem cell senescence? J. Clin. Invest., 2004, 113, 4-7).

Mitochondria play a central role in triggering apoptosis. The most critical mitochondrial events during apoptosis are the structural and functional remodelling of this organelle and subsequent release of apoptogenic proteins from the mitochondrial intermembrane space into the cytosol. These proteins include cytochrome C, Smac/DIABLO, AIF, Omi/HtrA2. Further, strong evidence exists to suggest that PTP opening may be an early event in the commitment to apoptosis.

The role of mitochondrial apoptosis in the aetiology of many diseases is well established and the increased rate of apoptosis typical of pathological stress conditions which are observed during myocardial infarction, renal ischemia, type I and Type II diabetes or neurodegenerative diseases always correlates with the Mitochondrial Permeability Transition and loss of mitochondrial integrity. Many of these disease states are characterized by significant increase of reactive oxygen species (ROS) that are known inducers of the MPT and apoptosis.

Some of the most important diseases resulting from opening of the MPTP are listed below:

Heart Infarction

In ischemic heart disease, sequential ischemia-reperfusion events occur resulting in myocardium cell death by necrosis and/or apoptosis and a role for the PTP and mitochondrial swelling in myocardial infarction has already been demonstrated (Solaini, G.; Harris, D. A. Biochemical dysfunction in heart mitochondria exposed to ischemia and reperfusion. Biochem. J., 2005, 390, 377-394). Disruption of mitochondrial integrity in cardiomyocytes through the deregulation of $Ca^{2+}$ and the production of ROS as a consequence of hypoxia-hyperoxia transition, is the major trigger of apoptosis during myocardial infarction. (Di Lisa, F.; Bernardi, P. Mitochondria and ischemia-reperfusion injury of the heart: Fixing a hole. Cardiovasc. Res., 2006, 70, 2, 191-199). Furthermore, cyclosporine A (CsA), a known inhibitor of the PTP, has been shown to improve recovery of baseline myocardial contractile function in human atrial tissue after experimental hypoxia and reperfusion.

Neurological Diseases and Stroke

PTP and mitochondrial swelling are also involved in neuronal cell death following degenerative diseases and in many high-prevalence conditions of brain damage such as hyperglycaemia, hypoglycaemia, stroke, ischemia, trauma and in experimental epilepsy (Pordan, J.; Cena, V.; Prehn, J. H. Mitochondrial control of neuron death and its role in neurodegenerative disorders. J. Physiol. Biochem., 2003, 59, 129-141; Li, P. A.; Uchino, H.; Elmer, E.; Siesjö, B. K. Amelioration by cyclosporin A of brain damage following 5 or 10 min of ischemia in rats subjected to preischemic hyperglycaemia. Brain Res., 1997, 753, 133-140; Folbergrova, J.; Li, P. A.; Uchino, H.; Smith, M. L.; Siesjö, B. K. Changes in the bioenergetic state of rat hippocampus during 2.5 min of ischemia, and prevention of cell damage by cyclosporin A in hyperglycaemic subjects. Exp. Brain Res., 1997, 114, 44-50; Friberg, H.; Ferrand-Drake, M.; Bengtsson, F.; Halestrap, A. P.; Wieloch, T. Cyclosporin A, but not FK 506, protects mitochondria and neurons against hypoglycaemic damage and implicates the mitochondrial permeability transition in cell death. J. Neurosci., 1998, 18, 5151-5159; Sims, N. R. and Anderson M. F. Mitochondrial contributions to tissue damage in stroke. Neurochem Int., 2002, 40, 511-26; Stavrovskaya I. G.; Narayanan M. V.; Zhang W.; Krasnikov B. F.; Heemskerk J.; Young S. S.; Blass J. P.; Brown A. M.; Beal M. F.; Friedlander R. M.; Kristal B. S. Clinically approved heterocyclics act on a mitochondrial target and reduce stroke-induced pathology. J Exp Med., 2004, 200, 211-22; Matsumoto, S.; Friberg, H.; Ferrand-Drake, M.; Wieloch, T. Blockade of the mitochondrial permeability transition pore diminishes infarct size in the rat after transient middle cerebral artery occlusion. J. Cereb. Blood Flow Metab., 1999, 19, 736-741 Scheff, S.

W.; Sullivan P. G. Cyclosporin A significantly ameliorates cortical damage following experimental traumatic brain injury in rodents. J. Neurotrauma, 1999, 16, 783-792; Kudin, A. P.; Debska-Vielhaber, G.; Vielhaber, S.; Elger, C. E.; Kunz, W. S. The mechanism of neuroprotection by topiramate in an animal model of epilepsy. Epilepsia, 2004, 45, 1478-1487). The beta-amyloid protein responsible for Alzheimer's disease induces oxidative stress and mitochondrial damage resulting in neuronal cell death indicating that mitochondrial dysfunction is associated with disease progression (Abramov, A. Y.; Canevari, L.; Duchen, M. R. Beta-amyloid peptides induce mitochondrial dysfunction and oxidative stress in astrocytes and death of neurons through activation of NADPH oxidase. J. Neurosci., 2004, 24, 565-575). In addition, the massive apoptosis occurring in the dopaminergic cells in Parkinson's disease has been causally linked to the MTP (Fiskum, G.; Starkov A.; Polster, B. M.; Chinopoulos, C. Mitochondrial mechanisms of neural cell death and neuroprotective interventions in Parkinson's disease. Ann. N.Y. Acad. Sci. 2003, 991, 111-119). Further, mitochondrial dysfunction leading to MPT has been characterized in Huntington's disease and amyotrophic lateral sclerosis (Tang, T. S.; Slow, E.; Lupu, V.; Stavrovskaya, I. G.; Sugimori, M.; Llinas, R.; Kristal, B. S.; Hayden, M. R.; Bezprozvanny, I. Disturbed $Ca^{2+}$ signaling and apoptosis of medium spiny neurons in Huntington's disease. Proc. Natl. Acad. Sci. U.S.A., 2005, 102, 2602-2607; Kirkinezos, I. G.; Hernandez, D.; Bradley, W. G.; Moraes, C. T. An ALS mouse model with a permeable blood-brain barrier benefits from systemic cyclosporine A treatment. J. Neurochem., 2004, 88, 821-826).

Diabetes

Diabetes, including type I and type II diabetes, induces damage and cell death by several mechanisms. Above all, hyperglycaemia itself is able to directly kill cells in a variety of tissues and in kidney, endothelial and retinal cell cultures (Allen, D. A.; Yaqoob, M. M.; Harwood, S. M. Mechanisms of high glucose-induced apoptosis and its relationship to diabetic complications. J. Nutr. Biochem., 2005, 16, 705-713). Diabetic retinopathy (DR) is one of the peripheral micro vascular complications strongly enhancing the morbidity of diabetic vascular diseases. This progressive condition leading to retinal neovascularization, the most common cause of blindness among young patients, has an enormous clinical significance in developed countries.

DR begins with an early pre-proliferative stage (background retinopathy) characterized by loss of capillary pericytes, progressive capillary closure, micro-aneurisms and retinal oedema. The subsequent retinal ischemia (or hypoxia) due to vessel occlusion, triggers abnormal retinal vessel growth. Neo-vessels extend along the inner surface of the retina and/or into the vitreous cavity and can lead to retinal detachment and haemorrhage. This stage is known as proliferative diabetic retinopathy (PDR). Hyperglycemic stress is considered a key factor in PDR since it induces increased production of vascular endothelium growth factor (VEGF) by retinal cells leading to neovascularization and causes cellular oxidative damage having repercussions on the mitochondria. In this view, mechanisms such as oxidative stress seem to play a major role in the pathogenic sequence. ROS, formed in higher amounts during diabetes, could trigger most of the pathologic intracellular pathways involved in PDR and it has been demonstrated that ROS are produced in retina during reperfusion following diabetes-induced ischemia. In addition, ROS have been implicated in the loss of micro-vascular pericytes, one of early alterations in the background diabetic retinopathy. A recent report demonstrated that retinal pericytes died through apoptosis if subjected to either hydrogen peroxide or ultraviolet radiation (UV), both of which are sources of ROS. Finally, oxidative stress was also correlated with incidence and progression of retinopathy of prematurity (ROP). The immature retina contains relatively low levels of antioxidants such as heme-oxygenase-1 and catalase. During hyper-oxygenation ROS are produced and, among other things, favour the generation of biologically active isoprostanes concurring to ischemia and, therefore, to the pathogenesis of ROP.

Inherited Dystrophies

Genetic disorders associated with tissue dysfunction and instability are often characterized by an increased rate of apoptosis. Indeed MPT was found to be causally involved in myocyte loss in some inherited myopathies. In particular inhibiting PTP with CsA treatment has been shown to reduce myofiber degeneration and to cure collagen type VI myopathy in mice (Irwin, W. A.; Bergamin, N.; Sabatelli, P.; Reggiani, C.; Megighian, A.; Merlini, L.; Braghetta, P.; Columbaro, M.; Volpin, D.; Bressan, G. M.; Bernardi, P.; Bonaldo, P. Mitochondrial dysfunction and apoptosis in myopathic mice with collagen VI deficiency. Nat. Genet., 2003, 35, 367-371).

Hepatitis

Liver can be damaged by different agents such as chemical poisons, inflammatory factors or viruses. In all cases, hepatocytes undergo massive apoptosis that is driven by the MPT (Haouzi, D.; Cohen, I.; Vieira, H. L.; Poncet, D.; Boya, P.; Castedo, M.; Vadrot, N.; Belzacq, A. S.; Fau, D.; Brenner, C.; Feldmann, G.; Kroemer, G. Mitochondrial permeability transition as a novel principle of hepatorenal toxicity in vivo. Apoptosis., 2002, 7, 395-405; Shirakata, Y.; Koike, K. Hepatitis B virus X protein induces cell death by causing loss of mitochondrial membrane potential. J. Biol. Chem., 2003, 278, 22071-22078). Furthermore, it has been reported that inhibiting PTP opening by treating mice with CsA strongly reduces liver damage in a rat model of TNF-α-dependent acute inflammatory hepatitis (Soriano, M. E.; Nicolosi, L.; Bernardi P. Desensitization of the permeability transition pore by cyclosporine A prevents activation of the mitochondrial apoptotic pathway and liver damage by tumour necrosis factor-alpha. J. Biol. Chem., 2004, 279, 36803-36808). Further, thiazole derivatives, as inhibitors of the PTP, were reported as being useful as medicines for preventing or treating hepatic cyrrhosis (Auget, M. et al., WO03009843).

In summary the mitochondrial permeability transition has been shown to be involved in the mechanism of apoptosis in a variety of disease states characterized by degenerative tissue damage. Hence pharmacological inhibition of the MPT represents an important approach for the prevention and treatment of a wide spectrum of diseases including cardiac infarction, neurological disease (due, for example, to traumatic insults and autoimmune reaction) and stroke, diabetes and diabetic complications such as diabetic retinopathy, inherited dystrophies and hepatitis (Kroemer, G. The mitochondrial permeability transition pore complex as a pharmacological target. Curr. Med. Chem., 2003, 10, 1469-1472; Mattson, M. P.; Kroemer, G. Mitochondria in cell death: novel targets for neuroprotection and cardioprotection. Trends Mol. Med., 2003, 9, 196-205).

BRIEF SUMMARY OF THE INVENTION

The main object of the present invention relates to the use of compounds of formula (I)

(I)

wherein $R^1$, $R^2$, $R^3$, and $R^4$ each independently represents: hydrogen; halo; hydroxy; ($C_1$-$C_6$) alkyl optionally substituted by hydroxy or ($C_1$-$C_4$) alkoxy; ($C_1$-$C_6$) haloalkyl; ($C_1$-$C_6$) alkoxy; or ($C_1$-$C_6$) haloalkoxy;

for the preparation of medicaments for the prevention and/or treatment of diseases resulting from opening of the MPTP which are characterized by degenerative tissue damages.

CHEMICAL BACKGROUND

Several compounds falling within formula (I) above are described in the scientific and/or patent literature. A non exhaustive list of compounds which have been previously disclosed is reported here below.

Augustin, M. et al. (Zeitschrift für Chemie, 1975, 15 (3), 102) describe reactions between aryl maleic anhydrides and monosubstituted anilines. Specifically, the synthesis of 1-(3-chlorophenyl)-3-(4-methylphenyl)-pyrrole-2,5-dione, 1-(3-chlorophenyl)-3-(4-methoxyphenyl)-pyrrole-2,5-dione, 1-(4-chlorophenyl)-3-(4-bromophenyl)-pyrrole-2,5-dione, 1-(2-methoxyphenyl)-3-(4-chlorophenyl)-pyrrole-2,5-dione, 3-(4-bromophenyl)-1-(4-methoxyphenyl)-pyrrole-2,5-dione, 1-(4-methoxyphenyl)-3-(4-methylphenyl)-pyrrole-2,5-dione, 1,3-bis-(4-methoxyphenyl)-pyrrole-2,5-dione, 1-(3-methylphenyl)-3-(4-methylphenyl)-pyrrole-2,5-dione and 1-(4-methylphenyl)-3-(4-bromophenyl)-pyrrole-2,5-dione are described.

Molchanov A. P. et al. (Russian Journal of Organic Chemistry (Translation of Zhurnal Organicheskoi Khimii), 2000, 36(8), 1139) describe reactions of diazoacetic acid esters with maleimides. Specifically, the following compounds are mentioned: 1-(4-methylphenyl)-3-(4-chlorophenyl)-pyrrole-2,5-dione and 1-(4-methoxyphenyl)-3-(4-chlorophenyl)-pyrrole-2,5-dione.

Almstrom, G. K. (Journal of the Chemical Society, Abstracts, 1916, 110 (I), 568) describes the synthesis of 1,3-diphenyl-pyrrole-2,5-dione and 1-(4-bromophenyl)-3-phenyl-pyrrole-2,5-dione.

Kwon, O. et al (J. Am. Chem. Soc., 2002, 124, 13402) describe the use of 1-(3-chlorophenyl)-3-phenyl-pyrrole-2,5-dione, in the synthesis of a library of 29 400 members.

Hebenbrock, K. F. (Liebigs Ann. Chem., 1978, 2, 320) discloses 1-(3,4-dichlorophenyl)-3-phenyl-pyrrole-2,5-dione, as a reagent for the preparation and studies of reactivity of 1-aryl-3-hydroxy-3-methyl-pyrrolidine-2,5-dione derivatives.

Molchanov, A. P. et al (Russian Journal of Organic Chemistry (Translation of Zhurnal Organicheskoi Khimii), 2002, 38(2), 259) describe the reaction of diphenyldiazomethane with substituted imides of maleic and itaconic acids. Specifically, 1-(2-chlorophenyl)-3-(4-methylphenyl)-pyrrole-2,5-dione is mentioned.

Umio, S. et al (JP43029950), disclose the synthesis of phenylmaleimides useful as bactericides. Specifically, the synthesis of 1-phenyl-3-(4-chlorophenyl)-pyrrole-2,5-dione and 1-phenyl-3-(4-methoxyphenyl)-pyrrole-2,5-dione are described.

Artico, M. et al (Farmaco, 1971, 26, 411) describe the synthesis of maleimides with antibacterial properties. Specifically, the synthesis of 1-(4-methylphenyl)-3-phenyl-pyrrole-2,5-dione is described.

Yuki, H. et al (Chemical & Pharmaceutical Bulletin, 1967, 15(8), 1101) describe the synthesis of compounds with antiviral properties. Specifically, the synthesis of 1-(4-chlorophenyl)-3-phenyl-pyrrole-2,5-dione, 1,3-bis-(4-methylphenyl)-pyrrole-2,5-dione, 1-(4-ethoxyphenyl)-3-(4-methylphenyl)-pyrrole-2,5-dione, 1-(4-ethoxyphenyl)-3-(4-chlorophenyl)-pyrrole-2,5-dione, 1-(4-ethoxyphenyl)-3-(4-methoxyphenyl)-pyrrole-2,5-dione, 1-phenyl-3-(3,4-dichlorophenyl)-pyrrole-2,5-dione, 1-phenyl-3-(4-methylphenyl)-pyrrole-2,5-dione, 1-(4-methylphenyl)-3-(4-methoxyphenyl)-pyrrole-2,5-dione, 1-(4-chlorophenyl)-3-(4-methoxyphenyl)-pyrrole-2,5-dione, 1,3-bis-(4-chlorophenyl)-pyrrole-2,5-dione and 1-(4-chlorophenyl)-3-(4-methylphenyl)-pyrrole-2,5-dione are disclosed.

Fujinami, A. et al (U.S. Pat. No. 3,743,654) describe the synthesis of maleimide derivatives as microbicides. Specifically, the synthesis of 1-(3,5-dichlorophenyl)-3-phenyl-pyrrole-2,5-dione, 1-(3,5-dichlorophenyl)-3-(2-chlorophenyl)-pyrrole-2,5-dione and 1-(3,5-dibromo-phenyl)-3-phenyl-pyrrole-2,5-dione are described.

Further compounds are disclosed in the chemical abstract database. Such derivatives are, for instance, 1-(2-chlorophenyl)-3-(4-chlorophenyl)-pyrrole-2,5-dione, 1-(3-chlorophenyl)-3-(4-chlorophenyl)-pyrrole-2,5-dione, 1-(3-chloro-2-methylphenyl)-3-(4-chlorophenyl)-pyrrole-2,5-dione, 1-(3,4-dichlorophenyl)-3-(4-chlorophenyl)-pyrrole-2,5-dione, 1-(3-bromophenyl)-3-(4-methylphenyl)-pyrrole-2,5-dione, 1-(4-bromophenyl)-3-(4-chlorophenyl)-pyrrole-2,5-dione, 1-(4-fluorophenyl)-3-phenyl-pyrrole-2,5-dione, 1-(4-iodophenyl)-3-phenyl-pyrrole-2,5-dione, 1-(2-methylphenyl)-3-(4-chlorophenyl)-pyrrole-2,5-dione, 1-(2,3-dimethyl-phenyl)-3-(4-chlorophenyl)-pyrrole-2,5-dione, 1-(3-methylphenyl)-3-(4-chlorophenyl)-pyrrole-2,5-dione, 1-(3-trifluoromethyl-phenyl)-3-(4-chlorophenyl)-pyrrole-2,5-dione and 1-(3-methoxyphenyl)-3-(4-chlorophenyl)-pyrrole-2,5-dione.

Further compounds are commercially available. Such derivatives are, for instance, 1-(4-trifluoromethoxyphenyl)-3-phenyl-pyrrole-2,5-dione, 1-(5-chloro-2-methoxyphenyl)-3-phenyl-pyrrole-2,5-dione, 1-(3-chloro-4-fluorophenyl)-3-phenyl-pyrrole-2,5-dione, 1-(4-fluorophenyl)-3-(4-chlorophenyl)-pyrrole-2,5-dione and 1-(3-trifluoromethylphenyl)-3-(4-methylphenyl)-pyrrole-2,5-dione.

Some compounds according to formula (I) which are known from the above cited prior art, have been reported to have a pharmaceutical activity.

For instance the following activities have been reported: 1-(4-methylphenyl)-3-phenyl-pyrrole-2,5-dione, as antibacterial, 1-(4-chlorophenyl)-3-phenyl-pyrrole-2,5-dione and 1,3-bis-(4-chlorophenyl)-pyrrole-2,5-dione as antiviral, 1-(3,5-dichlorophenyl)-3-(2-chlorophenyl)-pyrrole-2,5-dione, 1-(3,5-dibromophenyl)-3-phenyl-pyrrole-2,5-dione and 1-(3,5-dichlorophenyl)-3-phenyl-pyrrole-2,5-dione as microbicide.

To the best knowledge of the inventors, no pharmaceutical activity has been mentioned by any third parties for some compounds of formula (I) which have been disclosed in the above cited prior art.

Examples of said compounds are the following:
1-(5-chloro-2-methoxyphenyl)-3-phenyl-pyrrole-2,5-dione, 1-(4-trifluoromethoxyphenyl)-3-phenyl-pyrrole-2,5-dione, 1-(3-trifluoromethylphenyl)-3-(4-methylphenyl)-pyrrole-2,5-dione, 1-(3-chloro-4-fluorophenyl)-3-phenyl-pyrrole-2,5-dione, 1-(3-chlorophenyl)-3-phenyl-pyrrole-2,5-dione, 1-(3,4-dichlorophenyl)-3-phenyl-pyrrole-2,5-dione, 1-(3-methylphenyl)-3-(4-chlorophenyl)-pyrrole-2,5-dione, 1-(3,4-dichlorophenyl)-3-(4-chlorophenyl)-pyrrole-2,5-dione, 1-(3-chlorophenyl)-3-(4-chlorophenyl)-pyrrole-2,5-dione, 1,3-diphenyl-pyrrole-2,5-dione, 1-(3-chlorophenyl)-3-(4-methylphenyl)-pyrrole-2,5-dione and 1-(3-chlorophenyl)-3-(4-methoxyphenyl)-pyrrole-2,5-dione.

A further group of compounds of formula (I) above is considered to be novel.

Examples of these compounds are the following
1-(3-methoxyphenyl)-3-phenyl-pyrrole-2,5-dione, 1-(3-fluorophenyl)-3-phenyl-pyrrole-2,5-dione, 1-(3-iodophenyl)-3-phenyl-pyrrole-2,5-dione, 1-(3-bromophenyl)-3-phenyl-pyrrole-2,5-dione, 1-(3-trifluoromethoxyphenyl)-3-phenyl-pyrrole-2,5-dione, 1-(3-methylphenyl)-3-phenyl-pyrrole-2,5-dione, 1-(2-chlorophenyl)-3-phenyl-pyrrole-2,5-dione, 1-(4-bromo-3-fluorophenyl)-3-phenyl-pyrrole-2,5-dione, 1-(3-chloro-4-methylphenyl)-3-phenyl-pyrrole-2,5-dione, 1-(3-chloro-4-hydroxyphenyl)-3-phenyl-pyrrole-2,5-dione, 1-(4-fluoro-3-methylphenyl)-3-phenyl-pyrrole-2,5-dione, 1-(2,3-dimethylphenyl)-3-phenyl-pyrrole-2,5-dione, 1-(4-methoxy-2-methylphenyl)-3-phenyl-pyrrole-2,5-dione, 1-(3-trifluoromethylphenyl)-3-phenyl-pyrrole-2,5-dione, 1-(3-chlorophenyl)-3-(3-methylphenyl)-pyrrole-2,5-dione, 1-(3-chlorophenyl)-3-(4-fluorophenyl)-pyrrole-2,5-dione, 1-(3-chlorophenyl)-3-(3-fluorophenyl)-pyrrole-2,5-dione, 1-(3-chloro-4-fluorophenyl)-3-(3-fluorophenyl)-pyrrole-2,5-dione, 1-(3-chloro-4-fluorophenyl)-3-(4-fluorophenyl)-pyrrole-2,5-dione, 1-(3-chlorophenyl)-3-(4-hydroxyphenyl)-pyrrole-2,5-dione, 1-(3-chlorophenyl)-3-(4-bromophenyl)-pyrrole-2,5-dione, 1-(3-chlorophenyl)-3-(3-bromophenyl)-pyrrole-2,5-dione, 1-(3-chlorophenyl)-3-(2-fluorophenyl)-pyrrole-2,5-dione, 1-(3-chloro-4-fluorophenyl)-3-(2-fluorophenyl)-pyrrole-2,5-dione, 1-(2-fluorophenyl)-3-phenyl-pyrrole-2,5-dione, 1,3-bis-(4-fluorophenyl)-pyrrole-2,5-dione, 1-(3-fluorophenyl)-3-(4-fluorophenyl)-pyrrole-2,5-dione, 1-(3-trifluoromethylphenyl)-3-(4-methoxyphenyl)-pyrrole-2,5-dione, 1-(4-fluorophenyl)-3-(4-methoxyphenyl)-pyrrole-2,5-dione, 1-(2-methoxyphenyl)-3-(4-fluorophenyl)-pyrrole-2,5-dione, 1-(2-fluorophenyl)-3-(4-fluorophenyl)-pyrrole-2,5-dione, 1-(3-trifluoromethylphenyl)-3-(4-fluorophenyl)-pyrrole-2,5-dione, 1-(3,4-difluorophenyl)-3-phenyl-pyrrole-2,5-dione, 1-(3,4-difluorophenyl)-3-(4-methoxyphenyl)-pyrrole-2,5-dione, 1-(4-fluoro-2-methoxyphenyl)-3-phenyl-pyrrole-2,5-dione, 1-(4-fluoro-2-methoxyphenyl)-3-(4-fluorophenyl)-pyrrole-2,5-dione, 1-(3-chlorophenyl)-3-(3-fluoro-4-methoxyphenyl)-pyrrole-2,5-dione, 1-(3-chloro-4-fluorophenyl)-3-(3-fluoro-4-methoxyphenyl)-pyrrole-2,5-dione, 1-(3-fluorophenyl)-3-(3-fluoro-4-methoxyphenyl)-pyrrole-2,5-dione, 1-(3-fluorophenyl)-3-(3-fluoro-4-hydroxyphenyl)-pyrrole-2,5-dione, 1-(3-chloro-4-fluorophenyl)-3-(3-fluoro-4-hydroxy-phenyl)-pyrrole-2,5-dione, 1-(3,4-difluorophenyl)-3-(4-hydroxyphenyl)-pyrrole-2,5-dione, 1-(2-methoxyphenyl)-3-phenyl-pyrrole-2,5-dione and 1-(3-chlorophenyl)-3-(3-fluoro-4-hydroxyphenyl)-pyrrole-2,5-dione.

SUMMARY OF THE INVENTION

In view of the above, a first object of this invention relates to the use of compounds of formula (I)

wherein
$R^1$, $R^2$, $R^3$, and $R^4$ each independently represents: hydrogen; halo; hydroxy; ($C_1$-$C_6$) alkyl optionally substituted by hydroxy or ($C_1$-$C_4$) alkoxy; ($C_1$-$C_6$) haloalkyl; ($C_1$-$C_6$) alkoxy; and ($C_1$-$C_6$) haloalkoxy;

For the preparation of a medicament for the prevention and/or treatment of diseases resulting from opening of the MPTP which are characterized by degenerative tissue damage selected from diabetes and diabetic complications, neurological diseases and stroke, heart infarction, inherited dystrophies and hepatitis.

More particularly, the above said MPTP diseases, preferably include type I and type II diabetes and diabetic complications and neurological diseases and stroke; more preferably said MPTP diseases include diabetic vascular diseases such as diabetic retinopathy, and neurodegenerative disorders such as multiple sclerosis.

A further object of this invention is to provide a method of preventing and/or treating diseases resulting from opening of the MPTP which are characterized by degenerative tissue damage selected from diabetes and diabetic complications, neurological diseases and stroke, heart infarction, inherited dystrophies and hepatitis by administering from any such diseases an effective amount of a compound of formula (I) as defined above.

According to an aspect of this invention, a group of preferred compounds of formula (I) for the preparation of medicaments for the prevention and/or treatment of diseases resulting from opening of the MPTP which are characterized by degenerative tissue damages as defined above is represented by compounds of formula (I) wherein:
$R^1$, $R^2$, $R^3$, and $R^4$ each independently represents: hydrogen; halo; hydroxy; ($C_1$-$C_4$) alkyl optionally substituted by hydroxy or ($C_1$-$C_4$) alkoxy; ($C_1$-$C_4$) haloalkyl; ($C_1$-$C_4$) alkoxy; and ($C_1$-$C_4$) haloalkoxy.

According to another aspect of this invention, even more preferred compounds of formula (I) for the manufacture of a medicament for the prevention and/or treatment of diseases resulting from opening of the MPTP which are characterized by degenerative tissue damages as defined above are represented by compounds of formula (I) wherein: $R^1$, $R^2$, $R^3$, and $R^4$ each independently represents: hydrogen; fluoro; chloro; bromo; hydroxy; ($C_1$-$C_4$) alkyl optionally substituted by hydroxy or ($C_1$-$C_2$) alkoxy; $CF_3$; $CCl_3$; methoxy; ethoxy; isopropoxy; $OCF_3$; $OCHF_2$; and $OCH_2F$.

As used herein, the term "halo" or "halogen" is intended to include fluoro, chloro, bromo and iodo.

As used herein, the terms "($C_1$-$C_6$) alkyl", "($C_1$-$C_6$) haloalkyl", "($C_1$-$C_6$) alkoxy", "($C_1$-$C_6$) haloalkoxy", "($C_1$-$C_4$) alkyl", "($C_1$-$C_4$) haloalkyl", "($C_1$-$C_4$) alkoxy" and "($C_1$-$C_4$) haloalkoxy" are intended to include both branched and straight alkyl chains.

The branched alkyl moieties of the above radicals may contain one or more asymmetric carbon atoms which may give rise to enantiomers and/or diastereoisomers. With the term "stereoisomers" is herein intended all isomers of individual molecules that differ only in the configuration of their carbon atoms in the space. This term includes enantiomers and diastereoisomers.

The present invention includes all the possible stereoisomers of the compounds of formula (I) both as single isomers and their mixtures, including racemates. Some crystalline forms of the compounds may exist as polymorphs, which are also included in the present invention. Some of the compounds are solvated with water, and as such they are also intended to be encompassed within the scope of the invention.

Since, as stated above, to the best knowledge of the inventors, no pharmaceutical activity or medical use has been previously disclosed for some of the compounds already known which are falling within the general formula (I), a particular object of the invention relates to a compound selected from the group consisting of:

1-(5-chloro-2-methoxyphenyl)-3-phenyl-pyrrole-2,5-dione, 1-(4-trifluoromethoxyphenyl)-3-phenyl-pyrrole-2,5-dione, 1-(3-trifluoromethylphenyl)-3-(4-methylphenyl)-pyrrole-2,5-dione, 1-(3-chloro-4-fluorophenyl)-3-phenyl-pyrrole-2,5-dione, 1-(3-chlorophenyl)-3-phenyl-pyrrole-2,5-dione, 1-(3,4-dichlorophenyl)-3-phenyl-pyrrole-2,5-dione, 1-(3-methylphenyl)-3-(4-chlorophenyl)-pyrrole-2,5-dione, 1-(3,4-dichlorophenyl)-3-(4-chlorophenyl)-pyrrole-2,5-dione, 1-(3-chlorophenyl)-3-(4-chlorophenyl)-pyrrole-2,5-dione, 1,3-diphenyl-pyrrole-2,5-dione, 1-(3-chlorophenyl)-3-(4-methylphenyl)-pyrrole-2,5-dione and 1-(3-chlorophenyl)-3-(4-methoxyphenyl)-pyrrole-2,5-dione, for use as a medicament.

A further particular object of the invention relates to a novel compound selected from the group consisting of:

1-(3-methoxyphenyl)-3-phenyl-pyrrole-2,5-dione, 1-(3-fluorophenyl)-3-phenyl-pyrrole-2,5-dione, 1-(3-iodophenyl)-3-phenyl-pyrrole-2,5-dione, 1-(3-bromophenyl)-3-phenyl-pyrrole-2,5-dione, 1-(3-trifluoromethoxyphenyl)-3-phenyl-pyrrole-2,5-dione, 1-(3-methylphenyl)-3-phenyl-pyrrole-2,5-dione, 1-(2-chlorophenyl)-3-phenyl-pyrrole-2,5-dione, 1-(4-bromo-3-fluorophenyl)-3-phenyl-pyrrole-2,5-dione, 1-(3-chloro-4-methylphenyl)-3-phenyl-pyrrole-2,5-dione, 1-(3-chloro-4-hydroxyphenyl)-3-phenyl-pyrrole-2,5-dione, 1-(4-fluoro-3-methylphenyl)-3-phenyl-pyrrole-2,5-dione, 1-(2,3-dimethylphenyl)-3-phenyl-pyrrole-2,5-dione, 1-(4-methoxy-2-methylphenyl)-3-phenyl-pyrrole-2,5-dione, 1-(3-trifluoromethylphenyl)-3-phenyl-pyrrole-2,5-dione, 1-(3-chlorophenyl)-3-(3-methylphenyl)-pyrrole-2,5-dione, 1-(3-chlorophenyl)-3-(4-fluorophenyl)-pyrrole-2,5-dione, 1-(3-chlorophenyl)-3-(3-fluorophenyl)-pyrrole-2,5-dione, 1-(3-chloro-4-fluorophenyl)-3-(3-fluorophenyl)-pyrrole-2,5-dione, 1-(3-chloro-4-fluorophenyl)-3-(4-fluorophenyl)-pyrrole-2,5-dione, 1-(3-chlorophenyl)-3-(4-hydroxyphenyl)-pyrrole-2,5-dione, 1-(3-chlorophenyl)-3-(4-bromophenyl)-pyrrole-2,5-dione, 1-(3-chlorophenyl)-3-(3-bromophenyl)-pyrrole-2,5-dione, 1-(3-chlorophenyl)-3-(2-fluorophenyl)-pyrrole-2,5-dione, 1-(3-chloro-4-fluorophenyl)-3-(2-fluorophenyl)-pyrrole-2,5-dione, 1-(2-fluorophenyl)-3-phenyl-pyrrole-2,5-dione, 1,3-bis-(4-fluorophenyl)-pyrrole-2,5-dione, 1-(3-fluorophenyl)-3-(4-fluorophenyl)-pyrrole-2,5-dione, 1-(3-trifluoromethylphenyl)-3-(4-methoxyphenyl)-pyrrole-2,5-dione, 1-(4-fluorophenyl)-3-(4-methoxyphenyl)-pyrrole-2,5-dione, 1-(2-methoxyphenyl)-3-(4-fluorophenyl)-pyrrole-2,5-dione, 1-(2-fluorophenyl)-3-(4-fluorophenyl)-pyrrole-2,5-dione, 1-(3-trifluoromethylphenyl)-3-(4-fluorophenyl)-pyrrole-2,5-dione, 1-(3,4-difluorophenyl)-3-phenyl-pyrrole-2,5-dione, 1-(3,4-difluorophenyl)-3-(4-methoxyphenyl)-pyrrole-2,5-dione, 1-(4-fluoro-2-methoxyphenyl)-3-phenyl-pyrrole-2,5-dione, 1-(4-fluoro-2-methoxyphenyl)-3-(4-fluorophenyl)-pyrrole-2,5-dione, 1-(2-methoxyphenyl)-3-phenyl-pyrrole-2,5-dione, 1-(3-chlorophenyl)-3-(3-fluoro-4-methoxyphenyl)-pyrrole-2,5-dione, 1-(3-chloro-4-fluorophenyl)-3-(3-fluoro-4-methoxyphenyl)-pyrrole-2,5-dione, 1-(3-fluorophenyl)-3-(3-fluoro-4-methoxyphenyl)-pyrrole-2,5-dione, 1-(3-fluorophenyl)-3-(3-fluoro-4-hydroxyphenyl)-pyrrole-2,5-dione, 1-(3-chloro-4-fluorophenyl)-3-(3-fluoro-4-hydroxyphenyl)-pyrrole-2,5-dione, 1-(3,4-difluorophenyl)-3-(4-hydroxyphenyl)-pyrrole-2,5-dione, 1-(2-methoxyphenyl)-3-phenyl-pyrrole-2,5-dione, 1-(3-chlorophenyl)-3-(3,4-dimethoxyphenyl)-pyrrole-2,5-dione, 1-(3-chlorophenyl)-3-(3,4-dihydroxyphenyl)-pyrrole-2,5-dione and 1-(3-chlorophenyl)-3-(3-fluoro-4-hydroxyphenyl)-pyrrole-2,5-dione.

The biological activity of the compounds of formula (I) above as inhibitors of MPTP and their use for the manufacture of medicaments for the prevention and/or treatment of diseases resulting from opening of the MPTP which are characterized by degenerative tissue damages have been demonstrated through a series of in vitro and in vivo assays including a mitochondrial in vitro assay, and two in vivo mouse models: the retinopathy of prematurity (ROP) model of diabetic retinopathy and experimental autoimmune encephalomyelitis (EAE) as a model of multiple sclerosis.

The compounds of formula (I) of this invention can be obtained by reaction between anilines of formula (II) wherein $R^1$ and $R^2$ have the above definitions.

and compounds of formula (III) wherein $R^3$ and $R^4$ have the above definitions.

The compounds of formula (II) above are commercially available or can be easily synthesized by methods known by those skilled in the art.

The compounds of formula (III) above are commercially available or can be synthesized from compounds of formula (IV) wherein $R^3$ and $R^4$ have the above definitions.

(IV)

Such reaction can be conducted for example in acetic acid in presence of sulphuric acid at reflux.

The compounds of formula (IV) are obtainable by reaction between starting material of formula (V) wherein $R^3$ and $R^4$ have the above definitions and glyoxylic acid.

(V)

Such reaction is usually conducted at room temperature in methanol in the presence of potassium carbonate within two hours.

The compounds of formula (V) above are commercially available or can be easily synthesized by reaction between bromo benzyl derivatives of formula (VI)

(VI)

wherein $R^3$ and $R^4$ have the above definitions and KCN.

The compounds of formula (I) which are used for the manufacture of the medicaments according to the present invention are usually incorporated into pharmaceutical compositions which are suitable for achieving the intended purpose.

Accordingly, the compounds are contained in the above said pharmaceutical compositions in an amount which is effective for the disease to be prevented or treated. Typically, the compound may be administered to mammals, e.g. human at a dose varying from 0, 1 to 100 mg per kilogram of body weight per day, a determination of the optimal range for each individual being however within the skill of the art.

The pharmaceutical compositions, which are useful for administering the compounds of formula (I) according to this invention are in the form of oral, rectal, subcutaneous, intravenous, intramuscular, intraperitoneal, transdermal, transmucosal (including buccal, sublingual, transurethral, and rectal), topical, inhalation and ocular (including ocular implants, reservoir implants and injectable therapies such as intravitreal administration) routes or using any other route of administration.

The preparations that can be administered through oral route are usually in the form of both solid forms such as tablets, dragees and capsules and liquid forms such as syrups, emulsions and suspensions.

The solid forms contain together the active compound, suitable excipients and auxiliaries, e.g. fillers such as lactose, dextrose, saccharose, cellulose preparations and calcium phosphates, binders such as maize starch, potato starch, rice starch, gelatin, cellulose derivatives such as hydroxypropylmethyl cellulose, carboxymethylcellulose, arabic gum and polyvinyl pyrrolidone; lubricating agents such as silica, talc, stearic acid and/or its magnesium and calcium salts, and polyethylene glycol; disintegrating agents such as starch, agar, alginic acid or its salts, sodium starch glycolate and cross-linked polyvinyl pyrrolidone. Dyestuff, effervescing mixtures, wetting agents may be added to said solid form preparations which may be manufactured in a manner per se known, e.g. by combining the active compound(s) with the solid excipients, grinding the resulting mixture and processing said granules after adding suitable auxiliaries, if desired, into tablets, dragees or capsules. Sugar coating or film-coating processes may also be applied in the manufacture of the above said solid forms.

The solid oral formulations may be also in the form of sustained release formulations that can be prepared in conventional manner, for instance, by applying an enteric coating to tablets and granules.

The syrups may contain carriers like saccharose, glycerine, mannitol and/or sorbitol.

The suspension and emulsions may contain carriers such as natural gums, agar, sodium alginate, pectin, methylcellulose, carboxymethylcellulose and polyvinyl alcohol.

Pharmaceutical preparations which are suitable for rectal administration, e.g. suppositories, contain the active compound(s) together with a suppository base such as natural or synthetic triglycerides, cocoa butter, polyethylene glycol, paraffin hydrocarbons, polyoxyethylene, sorbitan fatty acid esters surfactants and lecithin.

The parenteral formulations suitable for subcutaneous and intramuscular administration include aqueous solutions as well as suspensions of the active compound(s) in an appropriate oily carrier. Suitable oily carriers include lipophilic vehicles such as fatty oils (e.g. sesame oil, olive oil), synthetic fatty acid esters, glycols (e.g. propylene glycol), triglycerides and polyethylene glycol.

The aqueous injection suspensions may contain also viscosity increasing substances, e.g. sorbitol, dextran, and sodium carboxymethylcellulose.

The preparations for intravenous injections or infusion usually contain sterile water as a carrier, preferably in the form of sterile aqueous isotonic saline solutions.

The compounds of the invention may also be administered via transdermal release. Typical transdermal formulations include conventional aqueous and non-aqueous vectors, such as creams, oils, lotions or pastes or can be provided as membranes or medicated plasters. In an embodiment, a compound of the invention is dispersed in a pressure-sensible plaster adhering to the skin. This formulation allows the compound to be spread from the plaster to the patient through the skin. In order to obtain a sustained drug release through the cutis, natural rubber and silicon can be used as pressure-sensitive adhesives.

The compounds of the invention can also be administered topically. Topical formulations may comprise, for example, an ointment, cream, gel, lotion, solution, paste or the like, and/or may be prepared so as to contain liposomes, micelles, and/or micrspheres. Ointments, as it is well known in the art of pharmaceutical formulation, are semisolid preparations that are typically based on petrolatum or other petroleum derivatives. Examples of ointments include oleaginous ointment bases, for example, vegetable oils, fats obtained from animals, and semisolid hydrocarbons obtained from petroleum, emulsifiable ointment bases, for example, hydroxystearin sulfate, anhydrous lanolin and hydrophilic petrolatum, emulsion ointment bases, for example, cetyl alcohol, glyceryl monostearate, lanolin and stearic acid and water-soluble ointment bases prepared from polyethylene glycols of varying molecular weight. (See, e.g., Remington: The Science and Practice of Pharmacy, Twentieth Ed., Lippincott Williams & Willcins: Philadelphia, 2000) Creams, as also well known to those skilled in the art, are viscous liquids of semisolid emulsions, and contain an oil phase, an emulsifier and an aqueous phase. The oil phase is generally comprised of petrolatum and a fatty alcohol such as cetyl or stearyl alcohol. The aqueous phase usually contains a humectant. The emulsifier in a cream formulation is chosen among nopn-ionic, anionic, catioknic or amphoteric surfactants. Single-phase gels contain organic macromolecules distributed substantially uniformly throughout the carrier liquid, which is typically aqueous, but also contain an alcohol and, optionally, an oil. Preferred gelling agents are crosslinked acrylic acid polymers (such as "carbomer" polymers, e.g. carboxypolyalkylenes that may be obtained commercially under the Carbopol® trademark. Also preferred are hydrophilic polymers such as polyethylene oxides, polyoxyethylene -polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. For the preparation of uniform gels, dispersing agents such as alcohol or glycerin can be added, or the gelling agent can be dispersed by trituration, mechanical mixing, and/or stirring.

EXAMPLES

General Methods

Commercially available reagents and solvents (HPLC grade) were used without further purification.

$^1$H NMR spectra were recorded on a Bruker 400 MHz AV spectrometer or Bruker DPX 250 MHz spectrometer or on a Bruker DPX 360 MHz spectrometer in deuterated solvents. Chemical shifts (δ) reported herein are in parts per million. Thin-layer chromatography (TLC) analysis was performed with Kieselgel 60 $F_{254}$ (Merck) plates and visualized using UV light.

Analytical HPLC-MS was performed on Agilent HP1100, Waters 600 or Waters 1525 LC systems using reverse phase Hypersil BDS C18 columns (5 μm, 2.1×50 mm), gradient 0-95% B (A=water/0.1% trifluoroacetic acid (TFA), B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software. For compounds of Examples 32 and 47 the HPLC-MS was performed on Agilent HP1100 system using reverse phase Waters Xterra® MS C8 columns (3.5 μm, 2.1× 50 mm), gradient 0-95% B (A=water/0.1% Formic acid, B=acetonitrile/0.1% Formic acid) over 7.0 min, flow=0.6 ml/min. UV spectra were recorded at 215 nm using a Waters 2996 diode array UV detector. Mass spectra were obtained over the range m/z 150 to 1000 at a sampling rate of 2 scans per second using a Waters ZQ mass spectrometer. Data were integrated and reported using OpenLynx and OpenLynx Browser software.

Example 1

1-(3-chlorophenyl)-3-(3-methylphenyl)-pyrrole-2,5-dione

A: glyoxylic acid, K$_2$CO$_3$, MeOH, reflux; B: HCO$_2$H, H$_2$SO$_4$, reflux; C: 3-chloro-phenylamine, AcOH, RT Step A: potassium 3-cyano-3-(3-methylphenyl)-acrylate To a stirred solution of (3-methylphenyl)-acetonitrile (21.6 ml, 165 mmol) in methanol (500 ml) were added glyoxylic acid hydrate (22.7 g, 247 mmol) and potassium carbonate (57.0 g, 412 mmol). The reaction mixture was stirred at room temperature for 2 hours followed by 3 hours at reflux. The precipitate was filtered off, washed with methanol (300 ml), dichloromethane (DCM) (300 ml) and then dried under air suction. The desired product was obtained as a white solid which was used in the next step without further purification.

Yield: 43 g

Mass spectrum (ES-MS (+ve)) 188 [M(free acid)+H]+, Retention time 1.82 min, 100% UV.

$^1$H-NMR (d$_6$-DMSO, 400 MHz) δ (ppm): 7.45-7.32 (2H, m), 7.30 (1H, t), 7.15 (1H, d), 7.05 (1H, s), 2.29 (3H, s).

Step B: (3-methylphenyl)-furan-2,5-dione

A suspension of potassium 3-cyano-3-(3-methylphenyl)-acrylate (0.69 g, 3 mmol), in 88% formic acid (14 ml) containing concentrated sulphuric acid (2 ml) was stirred at reflux and monitored by LC-MS until the starting material was consumed. The reaction mixture was cooled to room temperature and poured into ice/water. The resulting precipitate was recovered by filtration, washed with water (15 ml), heptane (15 ml) and air dried.

Yield: 270 mg (48%)

$^1$H-NMR (d$_6$-DMSO, 400 MHz) δ (ppm): 7.94-7.85 (2H, m), 7.72 (1H, s), 7.51-7.39 (2H, m), 2.40 (3H, s).

Step C: 1-(3-chlorophenyl)-(3-methylphenyl)-pyrrole-2,5-dione

To a stirred solution of (3-methylphenyl)-furan-2,5-dione (265 mg, 1.41 mmol) in acetic acid (5 ml) at room temperature was added 3-chloroaniline (149 μl, 1.41 mmol). The reaction mixture was heated to reflux and stirred for 3 hours. The reaction mixture was cooled to room temperature. The precipitate formed was filtered, re-suspended in water (15 ml) and recovered by filtration. The precipitate was washed with water (10 ml), heptane (10 ml) and dried under air suction followed by high vacuum.

Yield: 160 mg (38%)

Mass spectrum (ES-MS (+ve)) 298 [M+H]+, Retention time 2.52 min, 100% UV.

$^1$H-NMR (d$_6$-DMSO, 400 MHz) δ (ppm): 7.70-7.61 (2H, m), 7.35-7.10 (6H, m and 1H, s), 2.15 (3H, s).

EXAMPLES 2-42 were prepared according to the procedure described in scheme 1 using the required starting material (Step A) and the proper aniline (Step C) unless otherwise specified. The yields reported regard Step C in Scheme 1 unless otherwise specified.

Example 2

1-(3-chlorophenyl)-3-(4-fluorophenyl)-pyrrole-2,5-dione

Step A: potassium 3-cyano-3-(4-fluorophenyl)acrylate

The reaction was carried out at room temperature for 3 hours.

Yield: 2.2 g (38%)

Mass spectrum (ES-MS (+ve)) 192 [M(free acid)+H]+, Retention time 1.72 min, 100% UV.

$^1$H-NMR (d$_6$-DMSO, 400 MHz) δ (ppm): 7.69-7.60 (2H, m), 7.32-7.22 (2H, m), 7.03 (1H, s).

Step B: 3-(4-fluorophenyl)-furan-2,5-dione $^1$H-NMR (d$_6$-DMSO, 400 MHz) δ (ppm): 8.38-8.21 (2H, m), 7.90 (1H, s), 7.68-7.52 (2H, m).

Step C: 1-(3-chlorophenyl)-3-(4-fluorophenyl)-pyrrole-2,5-dione

Yield: 200 mg (85%)

Mass spectrum (ES-MS (+ve)) 302 [M+H]+, Retention time 2.44 min, 100% UV.

$^1$H-NMR (d$_6$-DMSO, 400 MHz) δ (ppm): 8.13-8.00 (2H, m), 7.50-7.39 (3H, m and 1H, s), 7.38-7.28 (3H, m).

Example 3

1-(3-chloro-4-fluorophenyl)-3-(4-fluorophenyl)-pyrrole-2,5-dione

Yield: 230 mg (92%)

Mass spectrum (ES-MS (+ve)) 320 [M+H]+, Retention time 2.52 min, 100% UV.

$^1$H-NMR (d$_6$-DMSO, 400 MHz) δ (ppm): 8.22-8.12 (2H, m), 7.75 (1H, d), 7.65 (1H, t), 7.53 (1H, s), 7.50-40 (3H, m).

Example 4

1,3-bis-(4-fluorophenyl)-pyrrole-2,5-dione

The title compound was prepared according to the procedure described in example 2. The solid recovered from filtration was further triturated with methanol (5 ml).

Yield: 207 mg (93%)

Mass spectrum (ES-MS (+ve)) 286 [M+H]+, Retention time 2.35 min, 98% UV.

$^1$H-NMR (d$_6$-DMSO, 400 MHz) δ (ppm): 8.23-8.10 (2H, m), 7.51-7.30 (6H, m and 1H, s).

Example 5

1-(3-fluorophenyl)-3-(4-fluorophenyl)-pyrrole-2,5-dione

The title compound was prepared according to the procedure described in example 2.

Yield: 181 mg (81%)

Mass spectrum (ES-MS (+ve)) 286 [M+H]+, Retention time 2.37 min, 98% UV.

$^1$H-NMR (d$_6$-DMSO, 250 MHz) δ (ppm): 8.21-8.05 (2H, m), 7.61-7.20 (6H, m and 1H, s).

Example 6

1-(2-methoxyphenyl)-3-(4-fluorophenyl)-pyrrole-2,5-dione

The title compound was prepared according to the procedure described in example 2. The solid recovered from filtration was further recrystallised from a 1:1 mixture of DCM/heptane (5 ml).

Yield: 132 mg (57%)

Mass spectrum (ES-MS (+ve)) 298 [M+H]$^+$, Retention time 2.30 min, 97% UV.

$^1$H-NMR (d$_6$-DMSO, 400 MHz) δ (ppm): 8.24-8.17 (2H, m), 7.56-7.42 (3H, m and 1H, s), 7.37 (1H, dd), 7.25 (1H, dd), 7.13 (1H, dt), 3.81 (3H, s).

Example 7

1-(2-fluorophenyl)-3-(4-fluorophenyl)-pyrrole-2,5-dione

The title compound was prepared according to the procedure described in example 2.

Yield: 195 mg (88%)

Mass spectrum (ES-MS (+ve)) 286 [M+H]$^+$, Retention time 2.34 min, 99% UV.

$^1$H-NMR (d$_6$-DMSO, 400 MHz) δ (ppm): 8.11-8.04 (2H, m), 7.53-725 (6H, m and 1H, s).

Example 8

1-(3-trifluoromethylphenyl)-3-(4-fluorophenyl)-pyrrole-2,5-dione

The title compound was prepared according to the procedure described in example 2.
The solid recovered from filtration was further recrystallised from a 1:1 mixture of DCM/heptane (5 ml).
Yield: 186 mg (71%)
Mass spectrum (ES-MS (+ve)) 377 [M+H+MeCN]+, Retention time 2.49 min, 100% UV. $^1$H-NMR (d$_6$-DMSO, 400 MHz) δ (ppm): 8.22-8.12 (2H, m), 7.85 (1H, s), 7.80-7.71 (3H, m), 7.52 (1H, s), 7.48-7.39 (2H, m).

Example 9

1-(3-chlorophenyl)-3-(3-fluorophenyl)-pyrrole-2,5-dione

Step A: potassium 3-cyano-3-(3-fluorophenyl)-acrylate

The reaction was carried out at room temperature.
Yield: 5.7 g
Mass spectrum (ES-MS (+ve)) 192 [M(free acid)+H]+, Retention time 1.72 min, 100% UV.
$^1$H-NMR (d$_6$-DMSO, 400 MHz) δ (ppm): 7.55-7.38 (3H, m), 7.27-7.20 (1H, m), 7.15 (1H, s).

Step B: 3-(3-fluorophenyl)-furan-2,5-dione $^1$H-NMR (d$_6$-DMSO, 400 MHz) δ (ppm): 7.92-7.79 (2H, m and 1H, s), 7.69-7.58 (1H, m), 7.51-7.39 (1H, m).

Step C: 1-(3-chlorophenyl)-3-(3-fluorophenyl)-pyrrole-2,5-dione

Yield: 210 mg (89%)
Mass spectrum (ES-MS (+ve)) 302 [M+H]+, Retention time 2.45 min, 95% UV.
$^1$H-NMR (d$_6$-DMSO, 400 MHz) δ (ppm): 8.14-8.03 (2H, m), 7.80-7.64 (4H, m and 1H, s), 7.61-7.51 (2H, m).

Example 10

1-(3-chloro-4-fluorophenyl)-3-(3-fluorophenyl)-pyrrole-2,5-dione

The title compound was prepared according to the procedure described in example 2.
Yield: 182 mg (73%)
Mass spectrum (ES-MS (+ve)) 320 [M+H]+, Retention time 2.54 min, 100% UV.
$^1$H-NMR (d$_6$-DMSO, 400 MHz) δ (ppm): 8.09-7.99 (2H, m), 7.80 (1H, m), 7.75-7.65 (2H, m and 1H, s), 7.60-7.55 (2H, m).

Example 11

1-(3-chlorophenyl)-3-(4-bromophenyl)-pyrrole-2,5-dione

Step A: potassium 3-(4-bromophenyl)-3-cyano-acrylate

The reaction was carried out at room temperature.
Yield: 11.0 g (not purified)
Mass spectrum (ES-MS (+ve)) 252, 254 [M(free acid)+H]+, Retention time 2.01 min, 100% UV.
$^1$H-NMR (d$_6$-DMSO, 400 MHz) δ (ppm): 7.49-7.40 (2H, m), 7.39-7.30 (2H, m), 6.97 (1H, s).

Step B: 3-(4-bromophenyl)-furan-2,5-dione

Yield: 5.4 g (84% over two steps)
$^1$H-NMR (d$_6$-DMSO, 400 MHz) δ (ppm): 8.02-7.96 (2H, m), 7.85-7.75 (2H, m and 1H, s).

Step C: 1-(3-chlorophenyl)-3-(4-bromophenyl)-pyrrole-2,5-dione

The residue was triturated with hot methanol to give the title compound.
Yield: 49 mg (37%)
Mass spectrum (ES-MS (+ve)) no ionisation, Retention time 2.57 min, 97% UV.
$^1$H-NMR (d$_6$-DMSO, 400 MHz) δ (ppm): 8.10-8.00 (2H, m), 7.88-7.70 (2H, m), 7.60-7.45 (3H, m and 1H, s), 7.40-7.35 (1H, m).

Example 12

1-(3-chlorophenyl)-3-(3-bromophenyl)-pyrrole-2,5-dione

Step A: potassium 3-(3-bromophenyl)-3-cyano-acrylate

The reaction was carried out at room temperature.
Yield: 12.5 g
Mass spectrum (ES-MS (+ve)) 252, 254 [M(free acid)+H]+, Retention time 1.98 min, 100% UV.
$^1$H-NMR (d$_6$-DMSO, 400 MHz) δ (ppm): 7.58 (1H, t), 7.47-7.38 (2H, m), 7.23 (1H, t), 7.04 (1H, s).

Step B: 3-(3-bromophenyl)-furan-2,5-dione

Yield: 4.7 g (73% over two steps)
$^1$H-NMR (d$_6$-DMSO, 400 MHz) δ (ppm): 8.23 (1H, s), 8.00 (1H, d), 7.84 (1H, s), 7.79 (1H, d), 7.55 (1H, t).

Step C: 1-(3-chlorophenyl)-3-(3-bromophenyl)-pyrrole-2,5-dione

The title compound was prepared according to the procedure described in example 2. The residue was triturated with hot methanol to give the title compound.
Yield: 45 mg (31%)
Mass spectrum (ES-MS (+ve)) no ionisation, Retention time 2.56 min, 100% UV.
$^1$H-NMR (d$_6$-DMSO, 250 MHz) δ (ppm): 8.30 (1H, s), 8.15-8.02 (1H, m), 7.80-7.70 (1H, m), 7.60 (1H, s), 7.58-7.46 (5H, m), 7.45-7.30 (1H, m).

Example 13

1-(3-chlorophenyl)-3-(2-fluorophenyl)-pyrrole-2,5-dione

Step A: potassium 3-cyano-3-(2-fluorophenyl)-acrylate

The reaction was carried out at room temperature.
Yield: 9 g

Mass spectrum (ES-MS (+ve)) 192 [M(free acid)+H]+, Retention time 1.81 min, 97% UV.
$^1$H-NMR (d$_6$-DMSO, 400 MHz) δ (ppm): 7.28-7.15 (2H, m), 7.10-7.01 (2H, m), 6.68 (1H, s).

Step B: 3-(2-fluorophenyl)-furan-2,5-dione

Yield: 2.1 g (30% over two steps)
$^1$H-NMR (d$_6$-DMSO, 400 MHz) δ (ppm): 8.11-8.00 (1H, m), 7.70-7.60 (1H, m), 7.52 (1H, s), 7.50-7.35 (2H, m).

Step C: 1-(3-chlorophenyl)-3-(2-fluorophenyl)-pyrrole-2,5-dione

Yield: 725 mg (92%)
Mass spectrum (ES-MS (+ve)) 302 [M+H]+, Retention time 2.45 min, 99% UV.
$^1$H-NMR (d$_6$-DMSO, 400 MHz) δ (ppm): 8.12-8.05 (1H, m), 7.68-7.37 (7H, m), 7.30 (1H, s).

Example 14

1-(3-chloro-4-fluorophenyl)-3-(2-fluorophenyl)-pyrrole-2,5-dione

Yield: 725 mg (87%)
Mass spectrum (ES-MS (+ve)) 320 [M+H]+, Retention time 2.46 min, 100% UV.
$^1$H-NMR (d$_6$-DMSO, 400 MHz) δ (ppm): 8.11-8.00 (1H, m), 7.79-7.70 (1H, m), 7.69-7.55 (2H, m), 7.52-7.38 (3H, m), 7.30 (1H, s).

Example 15

1-(3-methoxyphenyl)-3-phenyl-pyrrole-2,5-dione

The solid was further recrystallised from a 1:1 mixture of DCM/heptane (5 ml).
Yield: 310 mg (39%)
Mass spectrum (ES-MS (+ve)) 280 [M+H]+, Retention time 2.13 min, 96% UV.
$^1$H-NMR (d$_6$-DMSO, 250 MHz) δ (ppm): 8.13-8.02 (2H, m), 7.60-7.51 (3H, m), 7.47 (1H, s), 7.44-7.38 (1H, m), 7.03-6.93 (3H, m), 3.79 (3H, s).

Example 16

1-(3-fluorophenyl)-3-phenyl-pyrrole-2,5-dione

The title compound was prepared according to the procedure described in example 2. The solid was further recrystallised from a 1:1 mixture of DCM/heptane (5 ml).
Yield: 497 mg (65%)
Mass spectrum (ES-MS (+ve)) 268 [M+H]+, Retention time 2.16 min, 94% UV.
$^1$H-NMR (d$_6$-DMSO, 400 MHz) δ (ppm): 8.10-8.03 (2H, m), 7.61-7.51 (4H, m), 7.50 (1H, s), 7.36-7.24 (3H, m).

Example 17

1-(4-fluorophenyl)-3-phenyl-pyrrole-2,5-dione

The title compound was prepared according to the procedure described in example 2. The solid was further recrystallised from a 1:1 mixture of DCM/heptane (7 ml).
Yield: 106 mg (14%)
Mass spectrum (ES-MS (+ve)) 268 [M+H]+, Retention time 2.33 min, 100% UV.
$^1$H-NMR (d$_6$-DMSO, 400 MHz) δ (ppm): 7.96-7.89 (2H, m), 7.45-7.37 (3H, m), 7.36-7.28 (1H, s and 2H, m), 7.27-7.17 (2H, m).

Example 18

1-(3,4-difluorophenyl)-3-phenyl-pyrrole-2,5-dione

The title compound was prepared according to the procedure described in example 2. The solid was further recrystallised from a 1:1 mixture of DCM/heptane (7 ml).
Yield: 474 mg (58%)
Mass spectrum (ES-MS (+ve)) 286 [M+H]+, Retention time 2.38 min, 98% UV.
$^1$H-NMR (d$_6$-DMSO, 400 MHz) δ (ppm): 8.13-8.03 (2H, m), 7.68-7.48 (5H, m and 1H, s), 7.39-7.27 (1H, m).

Example 19

1-(3-iodophenyl)-3-phenyl-pyrrole-2,5-dione

Yield: 830 mg (77%)
Mass spectrum (ES-MS (+ve)) 376 [M+H]+, Retention time 2.28 min, 94% UV.
$^1$H-NMR (d$_6$-DMSO, 400 MHz) δ (ppm): 8.04-8.02 (2H, m), 7.82 (1H, s), 7.79 (1H, d), 7.58-7.51 (3H, m), 7.50-7.43 (2H, m), 7.32 (1H, t).

Example 20

1-(3-bromophenyl)-3-phenyl-pyrrole-2,5-dione

The solid was further recrystallised from a 1:1 mixture of DCM/heptane (5 ml).
Yield: 420 mg (45%)
Mass spectrum (ES-MS (+ve)) 328, 330 [M+H]+, Retention time 2.25 min, 93% UV.
$^1$H-NMR (d$_6$-DMSO, 400 MHz) δ (ppm): 8.05-8.03 (2H, m), 7.69 (1H, s), 7.64 (1H, d), 7.58-7.43 (6H, m).

Example 21

1-(3-trifluoromethoxyphenyl)-3-phenyl-pyrrole-2,5-dione

The solid was further recrystallised from a 1:1 mixture of DCM/heptane (5 ml).
Yield: 500 mg (52%)
Mass spectrum (ES-MS (+ve)) 334 [M+H]+, Retention time 2.28 min, 100% UV.
$^1$H-NMR (d$_6$-DMSO, 400 MHz) δ (ppm): 8.10-8.03 (2H, m), 7.69-7.64 (1H, t), 7.58-7.53 (3H, m), 7.52-7.49 (3H, m), 7.43 (1H, d).

Example 22

1-(3-methylphenyl)-3-phenyl-pyrrole-2,5-dione

The solid was further recrystallised from heptane (5 ml).
Yield: 310 mg (41%)
Mass spectrum (ES-MS (+ve)) 264 [M+H]+, Retention time 2.46 min, 97% UV.
$^1$H-NMR (d$_6$-DMSO, 400 MHz) δ (ppm): 8.02-7.97 (2H, m), 7.49-7.44 (3H, m), 7.40 (1H, s), 7.33 (1H, m), 7.20-7.09 (1H, m), 2.29 (3H, s).

Example 23

1-(2-chlorophenyl)-3-phenyl-pyrrole-2,5-dione

Yield: 716 mg (88%)
Mass spectrum (ES-MS (+ve)) 283 [M+H]+, Retention time 2.38 min, 92% UV.
$^1$H-NMR (d$_6$-DMSO, 400 MHz) δ (ppm): 8.11-8.03 (2H, m), 7.71 (1H, d), 7.62-7.51 (7H, m).

Example 24

1-(4-bromo-3-fluorophenyl)-3-phenyl-pyrrole-2,5-dione

Yield: 805 mg (81%)
Mass spectrum (ES-MS (+ve)) 346, 348 [M+H]+, Retention time 2.54 min, 97% UV.
$^1$H-NMR (d$_6$-DMSO, 400 MHz) δ (ppm): 8.10-8.03 (2H, m), 7.88 (1H, t), 7.58-7.52 (4H, m), 7.50 (1H, s), 7.29 (1H, d).

Example 25

1-(3-chloro-4-methylphenyl)-3-phenyl-pyrrole-2,5-dione

Yield: 780 mg (91%)
Mass spectrum (ES-MS (+ve)) 298, 300 [M+H]+, Retention time 2.55 min, 88% UV.
$^1$H-NMR (d$_6$-DMSO, 400 MHz) δ (ppm): 8.10-8.02 (2H, m), 7.57-7.46 (6H, m), 7.31 (1H, d), 2.38 (3H, s).

Example 26

1-(3-chloro-4-hydroxyphenyl)-3-phenyl-pyrrole-2,5-dione

Yield: 850 mg (99%)
Mass spectrum (ES-MS (+ve)) 300, 302 [M+H]+, Retention time 2.21 min, 90% UV.
$^1$H-NMR (d$_6$-DMSO, 400 MHz) δ (ppm): 10.40 (1H, s), 8.09-8.01 (2H, m), 7.45-7.49 (3H, m), 7.33 (1H, s), 7.31-7.29 (1H, m), 7.09-7.02 (1H, m), 6.98-6.92 (1H, m).

Example 27

1-(4-fluoro-3-methylphenyl)-3-phenyl-pyrrole-2,5-dione

The title compound was prepared according to the procedure described in example 2.
Yield: 397 mg (82%)
Mass spectrum (ES-MS (+ve)) 282 [M+H]+, Retention time 2.46 min, 91% UV.
$^1$H-NMR (d$_6$-DMSO, 400 MHz) δ (ppm): 8.13-8.04 (2H, m), 7.61-7.57 (3H, m), 7.51 (1H, s), 7.38 (1H, d), 7.34-7.29 (2H, m), 2.32 (3H, s).

Example 28

1-(2-fluorophenyl)-3-phenyl-pyrrole-2,5-dione

The title compound was prepared according to the procedure described in example 2.
Yield: 408 mg (89%)
Mass spectrum (ES-MS (+ve)) 268 [M+H]$^+$, Retention time 2.32 min, 90% UV.
$^1$H-NMR (d$_6$-DMSO, 400 MHz) δ (ppm): 8.09-8.02 (2H, m), 7.58-7.48 (5H, m and 1H, s), 7.47-7.40 (1H, m), 7.39-7.32 (1H, m).

Example 29

1-(2,3-dimethylphenyl)-3-phenyl-pyrrole-2,5-dione

The title compound was prepared according to the procedure described in example 2.
Yield: 355 mg (74%)
Mass spectrum (ES-MS (+ve)) 278 [M+H]+, Retention time 2.46 min, 88% UV.
$^1$H-NMR (d$_6$-DMSO, 400 MHz) δ (ppm): 8.21-8.15 (2H, m), 7.69-7.63 (3H, m), 7.61 (1H, s), 7.40 (1H, d), 7.33 (1H, t), 7.25 (1H, d), 2.44 (3H, s), 2.12 (3H, s).

Example 30

1-(4-methoxy-2-methylphenyl)-3-phenyl-pyrrole-2,5-dione

The title compound was prepared according to the procedure described in example 2.
Yield: 409 mg (81%)
Mass spectrum (ES-MS (+ve)) 294 [M+H]+, Retention time 2.39 min, 86% UV.
$^1$H-NMR (d$_6$-DMSO, 400 MHz) δ (ppm): 7.96-7.89 (2H, m), 7.43-7.38 (3H, m), 7.33 (1H, s), 7.06 (1H, d), 6.82-6.80 (1H, m), 6.75-6.71 (1H, m), 3.64 (3H, s), 1.95 (3H, s).

Example 31

1-(3-trifluoromethylphenyl)-3-phenyl-pyrrole-2,5-dione

The title compound was prepared according to the procedure described in example 2.
Yield: 439 mg (80%)
Mass spectrum (ES-MS (+ve)) 318 [M+H]+, Retention time 2.46 min, 98% UV.
$^1$H-NMR (d$_6$-DMSO, 400 MHz) δ (ppm): 8.07-8.01 (2H, m), 7.82 (1H, s), 7.79-7.70 (3H, m), 7.52-7.49 (3H, m), 7.48 (1H, s).

Example 32

1-(3-chlorophenyl)-3-(3,4-dimethoxyphenyl)-pyrrole-2,5-dione

Yield: 54 mg (46%)
Mass spectrum (ES-MS (+ve)) 344 [M+H]+, Retention time 4.84 min, 87% UV. (7 minute LC-MS method)
$^1$H-NMR (d$_6$-DMSO, 360 MHz): 7.87 (1H, dd), 7.71 (1H, d), 7.65-7.53 (3H, m), 7.50-7.45 (1H, m and 1H, s), 7.19 (1H, d), 3.91 (3H, s), 3.90 (3H, s)

Example 33

1-(3-trifluoromethylphenyl)-3-(4-methoxyphenyl)-pyrrole-2,5-dione

The title compound was prepared according to the procedure described in example 2.
Yield: 139 mg (82%)
Mass spectrum (ES-MS (+ve)) 348 [M+H]$^+$, Retention time 2.50 min, 90% UV.

$^1$H-NMR (d$_6$-DMSO, 250 MHz) δ (ppm): 8.10 (2H, d), 7.90-7.70 (4H, m), 7.39 (1H, s), 7.10 (2H, d), 3.85 (3H, s).

Example 34

1-(4-fluorophenyl)-3-(4-methoxyphenyl)-pyrrole-2,5-dione

The title compound was prepared according to the procedure described in example 2.
Yield: 95 mg (65%)
Mass spectrum (ES-MS (+ve)) 298 [M+H]$^+$, Retention time 2.35 min, 92% UV.
$^1$H-NMR (d$_6$-DMSO, 250 MHz) δ (ppm): 8.10 (2H, d), 7.51-7.28 (4H, m and 1H, s), 7.11 (2H, d), 3.86 (3H, s).

Example 35

1-(3,4-difluorophenyl)-3-(4-methoxyphenyl)-pyrrole-2,5-dione

The title compound was prepared according to the procedure described in example 2.
Yield: 280 mg (91%)
Mass spectrum (ES-MS (+ve)) 316 [M+H]$^+$, Retention time 2.40 min, 97% UV.
$^1$H-NMR (d$_6$-DMSO, 400 MHz) δ (ppm): 8.14 (2H, d), 7.71-7.58 (2H, m), 7.40 (1H, s), 7.38-7.32 (1H, m), 7.16 (2H, d), 3.89 (3H, s).

Example 36

1-(3-chlorophenyl)-3-(4-hydroxyphenyl)-pyrrole-2,5-dione

The title compound was prepared according to the procedure described in example 2.
Yield: 92 mg (67%)
Mass spectrum (ES-MS (+ve)) 300 [M+H]+, Retention time 2.22 min, 94% UV.
$^1$H NMR (d$_6$-DMSO, 400 MHz) δ (ppm): 10.30 (1H, s), 8.00 (2H, d), 7.56-7.45 (3H, m), 7.40 (1H, d), 7.24 (1H, s), 6.91 (2H, d).

Example 37

1-(3-chlorophenyl)-3-(3-fluoro-4-methoxyphenyl)-pyrrole-2,5-dione

Step A: potassium 3-cyano-3-(3-fluoro-4-methoxyphenyl)-acrylate

The title compound was prepared according to the procedure described in example 2.
Yield: 15.5 g
Mass spectrum (ES-MS (+ve)) 222 [M(free acid)+H]$^+$, Retention time 1.74 min, 100% UV.
$^1$H-NMR (d$_6$-DMSO, 400 MHz) δ (ppm): 7.28-7.10 (4H, m), 3.96 (3H, s, Me).

Step B: 1-(3-chlorophenyl)-3-(3-fluoro-4-methoxyphenyl)-furan-2,5-dione

Yield: 1.7 g (32% over two steps)
$^1$H-NMR (d$_6$-DMSO, 250 MHz) δ (ppm): 8.00-7.90 (2H, m), 7.65 (1H, s, alkene CH), 7.38 (1H, t), 3.94 (3H, s, Me).

Step C: 1-(3-chlorophenyl)-3-(3-fluoro-4-methoxyphenyl)-pyrrole-2,5-dione

The title compound was prepared according to the procedure described in example 2.
Yield: 132 mg (59%)
Mass spectrum (ES-MS (+ve)) no ionisation, Retention time 4.87 min, 97% UV.
$^1$H-NMR (d$_6$-DMSO, 400 MHz) δ (ppm): 8.02-7.94 (2H, m), 7.58-7.46 (3H, m), 7.44-7.32 (1H, s and 2H, m), 3.93 (3H, s, Me).

Example 38

1-(3-chloro-4-fluorophenyl)-3-(3-fluoro-4-methoxyphenyl)-pyrrole-2,5-dione

The title compound was prepared according to the procedure described in example 2. The solid was further recrystallised from methanol (5 ml).
Yield: 131 mg (55%)
Mass spectrum (ES-MS (+ve)) no ionisation, Retention time 2.46 min, 89% UV.
$^1$H-NMR (d$_6$-DMSO, 400 MHz) δ (ppm): 8.02-7.94 (2H, m), 7.70 (1H, dd), 7.59 (1H, t), 7.48-7.42 (1H, m and 1H, s), 7.35 (1H, t), 3.93 (3H, s).

Example 39

1-(2-methoxyphenyl)-3-phenyl-pyrrole-2,5-dione

The title compound was prepared according to the procedure described in example 2. The solid was further recrystallised from a 1:1 mixture of DCM/heptane (5 ml).
Yield: 120 mg (15%)
Mass spectrum (ES-MS (+ve)) 280 [M+H]$^+$, Retention time 4.47 min, 98% UV.
$^1$H-NMR (d$_6$-DMSO, 400 MHz) δ (ppm): 8.09-8.01 (2H, m), 7.57-7.51 (3H, m), 7.50-7.43 (1H, m and 1H, s), 7.31 (1H, dd), 7.19 (1H, dd), 7.06 (1H, dt), 3.75 (3H, s).

Example 40

1-(4-fluoro-2-methoxyphenyl)-3-phenyl-pyrrole-2,5-dione

The title compound was prepared according to the procedure described in example 2. The solid was further triturated with methanol (5 ml).
Yield: 74 mg (43%)
Mass spectrum (ES-MS (+ve)) 298 [M+H]$^+$, Retention time 2.32 min, 88% UV.
$^1$H-NMR (d$_6$-DMSO, 400 MHz) δ (ppm): 8.09-8.01 (2H, m), 7.58-7.50 (3H, m), 7.47 (1H, s, alkene CH), 7.39 (1H, dd), 7.13 (1H, dd), 6.92 (1H, dt), 3.77 (3H, s, Me).

Example 41

1-(4-fluoro-2-methoxyphenyl)-3-(4-fluorophenyl)-pyrrole-2,5-dione

The title compound was prepared according to the procedure described in example 2. The solid was further triturated with methanol (5 ml).
Yield: 123 mg (68%)
Mass spectrum (ES-MS (+ve)) 316 [M+H]$^+$, Retention time 4.58 min, 100% UV.

$^1$H-NMR (d$_6$-DMSO, 400 MHz) δ (ppm): 8.18-8.10 (2H, m), 7.47 (1H, s), 7.45-7.35 (3H, m), 7.13 (1H, dd), 6.92 (1H, dt), 3.77 (3H, s, Me).

Example 42

1-(3-fluorophenyl)-3-(3-fluoro-4-methoxyphenyl)-pyrrole-2,5-dione

The title compound was prepared according to the procedure described in example 2.

Yield: 123 mg (58%)

Mass spectrum (ES-MS (+ve)) 316 [M+H]$^+$, Retention time 4.68 min, 100% UV.

$^1$H-NMR (d$_6$-DMSO, 250 MHz) δ (ppm): 8.05-7.95 (2H, m), 7.64-7.50 (1H, m), 7.45 (1H, s), 7.42-7.23 (4H, m), 3.94 (3H, s).

Example 43

1-(3-chlorophenyl)-3-(3-fluoro-4-hydroxyphenyl)-pyrrole-2,5-dione

Boro tribromide (52.5 ml, 0.55 mmol) was added dropwise to a solution of 1-(3-chlorophenyl)-3-(3-fluoro-4-methoxyphenyl)-pyrrole-2,5-dione (example 39; 175 mg, 0.53 mmol) in dichloromethane (5 ml) at room temperature under nitrogen. The solution was stirred for 6 hours at room temperature. The reaction was then poured into ice-water (5 ml) and stirred for further 30 min. The by was filtered off, washed with water (10 ml), and dried with suction.

Yield: 123 mg (73%)

Mass spectrum (ES-MS (+ve)) 318 [M+H]$^+$, Retention time 4.42 min, 99% UV.

$^1$H NMR (d$_6$-DMSO, 400 MHz) δ (ppm): 10.84 (1H, s), 7.94 (1H, dd), 7.85 (1H, dd), 7.58-7.46 (3H, m), 7.42-7.36 (1H, m), 7.33 (1H, s), 7.09 (1H, t).

EXAMPLES 44-47 were prepared according to the procedure described in example 43 for 1-(3-chlorophenyl)-3-(3-fluoro-4-hydroxyphenyl)-pyrrole-2,5-dione starting from the required methoxy derivative.

Example 44

1-(3-chloro-4-fluorophenyl)-3-(3-fluoro-4-hydroxyphenyl)-pyrrole-2,5-dione

The solid was further recrystallised from methanol (2 ml).

Yield: 22 mg (46%)

Mass spectrum (ES-MS (+ve)) no ionisation, Retention time 4.46 min, 89% UV.

$^1$H NMR (d$_6$-DMSO, 400 MHz) δ (ppm): 10.84 (1H, s), 7.94 (1H, dd), 7.85 (1H, dd), 7.69 (1H, dd), 7.58 (1H, t), 7.49-7.41 (1H, m), 7.34 (1H, s), 7.09 (1H, t).

Example 45

1-(3-fluorophenyl)-3-(3-fluoro-4-hydroxyphenyl)-pyrrole-2,5-dione

Yield: 21 mg (49%)

Mass spectrum (ES-MS (+ve)) no ionisation, Retention time 4.22 min, 90% UV.

$^1$H NMR (d$_6$-DMSO, 400 MHz) δ (ppm): 10.83 (1H, s), 7.95 (1H, dd), 7.85 (1H, dd), 7.60-7.51 (1H, m), 7.37-7.22 (3H, m and 1H, s), 7.09 (1H, t).

Example 46

1-(3,4-difluorophenyl)-3-(4-hydroxyphenyl)-pyrrole-2,5-dione

Yield: 116 mg (56%)

Mass spectrum (ES-MS (+ve)) no ionisation, Retention time 4.24 min, 98% UV.

$^1$H NMR (d$_6$-DMSO, 250 MHz) δ (ppm): 10.30 (1H, s), 8.00 (2H, d), 7.70-7.50 (2H, m), 7.35-7.22 (1H, m and 1H, s), 6.92 (2H, d).

Example 47

1-(3-chlorophenyl)-3-(3,4-dihydroxyphenyl)-pyrrole-2,5-dione

Yield: 23 mg (57%)

Mass spectrum (ES-MS (+ve)) 316 [M+H]+, Retention time 4.23 min, 96% UV. (7 minute LC-MS method)

$^1$H NMR (d$_6$-DMSO, 400 MHz): 9.95 (2H, broad s), 7.70-7.48 (5H, m), 7.44-7.39 (1H, m), 7.17 (1H, s), 6.89 (1H, d).

The following compounds are commercially available or described in the literature.

Example 48

1-(3-chlorophenyl)-3-(4-methoxyphenyl)-pyrrole-2,5-dione (Augustin, M.; Koehler, M. Synthesis of 2-aryl maleimides. Zeitschrift fur Chemie, 1975, 15 (3), 102)

Example 49

1,3-diphenylpyrrole-2,5-dione (Almstrom, G. K.
Some derivatives of pyrrole. III. Journal of the Chemical Society, Abstracts (1916), 110(I), 568)

Example 50

1-(4-chlorophenyl)-3-phenyl-pyrrole-2,5-dione (Yuki, H.; Yamamoto, T.; Tohira, Y.; Aoki, B.; Aoki, B.; Kano, T.; Yamazaki, T. Antiviral agents. II. Synthesis and biological activity of maleimide derivatives. Chemical & Pharmaceutical Bulletin (1967), 15(8), 1101-1106)

Example 51

1-(3,4-dichlorophenyl)-3-phenyl-pyrrole-2,5-dione (Hebenbrock, K. F. Preparation and reaction of 1-aryl-3-hydroxy-3-methyl-2,5-pyrrolidinediones. Justus Liebigs Annalen der Chemie 1978, (2), 320-336)

Example 52

1-(4-methylphenyl)-3-phenyl-pyrrole-2,5-dione (Artico, M.; Filacchioni, G.; Nacci, V.; Chimenti, F. Synthesis of pyrrolnitrin analogs. III. Preparation and antibacterial properties of 1,3-diaryl-substituted maleimides. Farmaco, Edizione Scientifica 1971, 26(5), 411-423)

Example 53

1-(3-methylphenyl)-3-(4-chlorophenyl)-pyrrole-2,5-dione, Chemical block: A0846/0039618, Moscow, Russia

Example 54

1-(3,4-dichlorophenyl)-3-(4-chlorophenyl)-pyrrole-2,5-dione, Chemical block: A1495/0065580

Example 55

1-(3-chlorophenyl)-3-(4-chlorophenyl)-pyrrole-2,5-dione, Chembridge: 5630429, San Diego, USA

Example 56

1,3-bis-(4-chlorophenyl)-pyrrole-2,5-dione, Chembridge: 5633406

Example 57

1-(3-chlorophenyl)-3-(4-methylphenyl)-pyrrole-2,5-dione (Augustin, M.; Koehler, M. Synthesis of 2-aryl maleimides. Zeitschrift fur Chemie, 1975, 15 (3), 102)

Example 58

1-(5-chloro-2-methoxyphenyl)-3-phenyl-pyrrole-2,5-dione, Maybridge: 512623, Tintagel, UK

Example 59

1-(4-trifluoromethoxyphenyl)-3-phenyl-pyrrole-2,5-dione, Maybridge: S13120, Tintagel, UK

Example 60

1-(3-trifluoromethylphenyl)-3-(4-methylphenyl)-pyrrole-2,5-dione, Chembridge: 5632689, San Diego, USA

Example 61

1-(3-chloro-4-fluorophenyl)-3-phenyl-pyrrole-2,5-dione, Maybridge: 509209, Tintagel, UK

Example 62

1-(4-fluorophenyl)-3-(4-chlorophenyl)-pyrrole-2,5-dione, Chembridge: 5628990, San Diego, USA

Example 63

1-(3-chlorophenyl)-3-phenyl-pyrrole-2,5-dione, Maybridge: 509579, Tintagel, UK

Mitochondrial In Vitro Assay: Method and Results

The mitochondrial in vitro assay is based on the characteristics of mitochondrial organelles which allow the study of mitochondrial function in reductive sub-cellular in vitro systems. It is possible to investigate many mitochondrial processes in isolated mitochondrial suspension obtained from different tissues.

The ability of isolated mitochondria to uptake calcium from outside is a direct measure of mitochondrial integrity and functioning. Indeed MPT impairs the ability of mitochondria to upload calcium through specific channels that require an intact organelle structure. The assay takes advantage of this phenomenon to evaluate the ability of the invention compounds to interfere with MPT on isolated mitochondria.

Mouse Liver Mitochondrial Preparation

Mitochondria were prepared from the livers of male 129 or C57/B6 mouse weighing 20-25 g. The animals were sacrificed by cervical dislocation. The livers were isolated and placed in ice-cold 0.25 M sucrose, 10 mM Tris-HCl, 0.1 mM ethylene-bis(oxoethylenenitrilo)tetraacetic acid (EGTA), pH 7.4 The livers were rinsed three-four times with ice-cold medium, minced with scissor and passed through a manual Potter homogenizer kept in an ice-water bath. The homogenate was diluted to 50 ml per liver, and unbroken cells and nuclei were sedimented by centrifugation at 900×g in a Beckman Avanti™ J-25 refrigerated centrifuge kept at 4° C. for 10 min. The supernatant was carefully decanted and centrifuged at 7000×g in the same centrifuge for 10 min. The supernatant was discarded and the mitochondrial pellets were carefully resuspended in ice-cold isolation medium and spun as above.

The resulting mitochondrial pellets were resuspended in a small amount of ice-cold isolation medium, and stored on ice. Mitochondria protein content was determined with the biuret assay.

Calcium Retention Capacity (CRC)

The mitochondrial $Ca^{2+}$ retention capacity (CRC) is a sensitive measure of the propensity of mitochondria to open the PTP after $Ca^{2+}$ uptake. Since mitochondria are bidirectionally permeable to $Ca^{2+}$ owing to the presence of a $Ca^{2+}$ uniporter in their inner membrane, the mitochondrial membrane potential ($\Delta\psi m$) is responsible for the $Ca^{2+}$ accumulation in the mitochondrial matrix and consequent $Ca^{2+}$ gradient. Any drop in $\Delta\psi m$, such as depolarization caused by $H^+$ influx during PTP opening, is expected to result in a redistribution of $Ca^{2+}$ between the intra and extra-mitochondrial spaces, during which $Ca^{2+}$ uses all available routes through the mitochondrial membrane.

CRC of mitochondrial preparations was assessed fluorimetrically in the presence of the fluorescent $Ca^{2+}$ indicator Calcium Green-5N (excitation-emission: 505-535 nm) with a Perkin-Elmer LS 55 spectrofluorimeter equipped with a magnetic stirrer and thermostatic control set to 25° C. (Ichas, F.; Jouaville, L. S.; Mazat, J. P. Mitochondria are excitable organelles capable of generating and conveying electrical and calcium signal. Cell., 1997, 89, 1145-1153). Calcium Green-5N is a fluorometric probe that is not permeable to membranes and when added to a mitochondrial suspension is able to detect the presence of $Ca^{2+}$ in the extra-mitochondrial medium. Mitochondria were loaded with a train of 10 μM $Ca^{2+}$ pulses at 1 min intervals. Under these conditions mitochondria took up actively and retained $Ca^{2+}$ until a point at which mitochondria underwent a fast process of $Ca^{2+}$ release due to the opening of the PTP. The number of calcium pulses (final concentration of calcium) required to open the PTP is the mitochondrial CRC. This $Ca^{2+}$ loading protocol thus provides a convenient and sensitive assay for measuring PTP opening and it is used to assess the ability of the compounds of the invention to inhibit PTP opening. Compounds were added directly to the mitochondrial solution 1 min. prior to the start of calcium pulsing and the number of calcium pulses required to open the PTP was determined. The ratio between the amount of calcium (calculated from the number of calcium pulses) required to trigger swelling in the presence of the compound with respect to that required to induce swelling in the absence of the compound is a measure of the protective effect of the compound. This value is called the CRC efficacy and the results obtained from several compounds of the invention are reported in table 1.

TABLE 1

CRC assay results

| Example Nbr. | CRC efficacy |
|---|---|
| Example 2 | 2.5 |
| Example 9 | 2.75 |
| Example 10 | 2.27 |
| Example 13 | 2 |
| Example 14 | 2.22 |
| Example 20 | 2.33 |

TABLE 1-continued

CRC assay results

| Example Nbr. | CRC efficacy |
|---|---|
| Example 22 | 2.57 |
| Example 31 | 2 |
| Example 36 | 1.87 |
| Example 48 | 2.11 |
| Example 53 | 2.17 |
| Example 55 | 2.33 |
| Example 57 | 2.66 |
| Example 58 | 1.86 |
| Example 61 | 2.83 |
| Example 63 | 2.5 |

ROP Assay: Methods and Results

Retinal neo-vascularisation was assessed in a mouse retinopathy of prematurity (ROP) model of ischemia-induced retinal neo-vascularisation. In rodents, retinal vascularisation is generally completed by post-natal day 14 (P14). Oxygen treatment during the second week of life partially causes vaso-obliteration of immature retinal vessels around the optic disk and it blocks subsequent vascular development of the deep retinal layers. When oxygen treatment is stopped, the ischemia of the retina triggers abnormal vessel growth, i.e., retinal neovascularisation.

At postnatal day 7 (P7), newborn mice were exposed to 75% $O_2$ for 5 days in an oxygen incubator. To avoid the effect of carbon dioxide on rat retinas (Holmes, J. M.; Zhang, S.; Leske, D. A.; Lanier, W. L. Carbon dioxide-induced retinopathy in the neonatal rat. Curr. Eye Res., 1998, 17, 608-616), a $CO_2$ absorbent was placed into the incubator (Sodasorb; GRACE, Epernon, France). Oxygen concentration was monitored by an Oxygen Monitor (Miniox III; Catalyst Research, MD). Litters raised in room air (21% O2) were control animals.

At day 12 (P12) animals were removed from the oxygen exposure chamber and injected intra-vitreously with a Hamilton syringe with compounds or vehicle solution. Few mice from both ROP and controls were randomly chosen, anesthetized and then perfused through the left ventricle with 1 ml, of fluorescein isothiocyanate-dextran (2×106 molecular weight) 50 mg/ml in PBS (Sigma Chemical Co., St. Louis, Mo.). The remaining animals of each group were maintained in room air for 5 additional days (P17) and then fluorescein-perfused as described. After perfusion, the eyes were enucleated and then fixed in 4% paraformaldehyde for 24 h at 4° C. The cornea, lens and vitreous were surgically removed; retinas were gently dissected and peripheral retinas were cut to allow flat mounting with glycerol-gelatine:. Flat-mounted retinas were photographed by fluorescence microscopy (Zeiss Axioplan Thornwood, N.Y.) and by computer-imaging (KS300, Kontron Electronik GmbH, Germany) retinal images captured.

Two groups of newborns, subjected to ROP, were injected at P12 with the compound. 1-(3-chlorophenyl)-3-phenyl-pyrrole-2,5-dione of example 63 dissolved in DMSO or DMSO alone (vehicle), to get a final concentration of approximately 1 or 2 or 4 microM of the compound in the vitreum.

Fluorangiographic analysis at p17 revealed a significant reduction of the neovascularization upon treatment with the compound.

Figure 1:
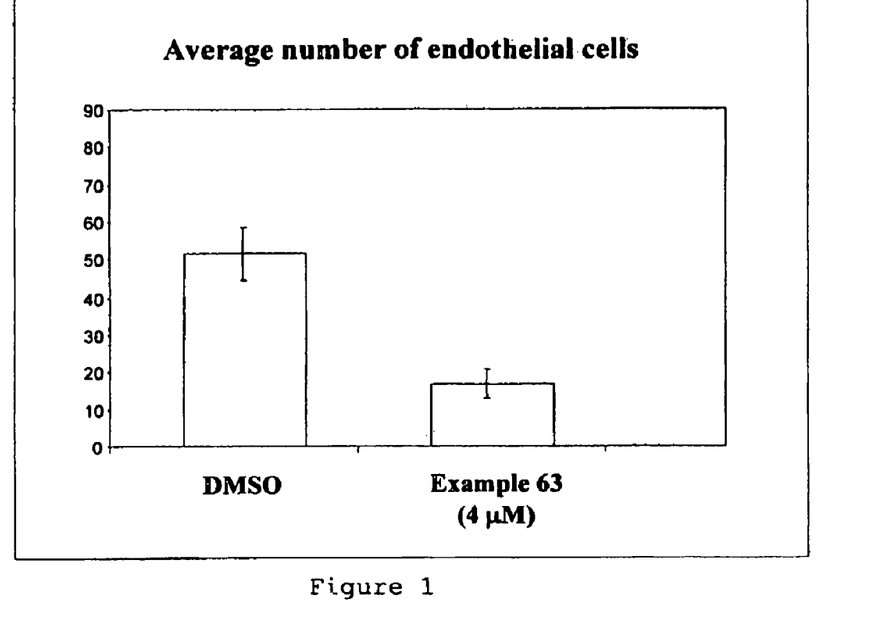
FIG. 1 shows the average number of endothelial cells per section obtained from one experiment representative of four, each involving 4 different mice.

Eyes from the same groups, at p17, were fixed and sections were prepared and stained with hematoxylin and eosin to quantify the amount of endothelial cells developed. The graph below reports the average number of endothelial cells per section obtained from one experiment representative of four, each involving 4 different mice (FIG. 1).

The treatment with the above compound significantly reduces the number of endothelial cells present in the eye after the ROP challenge, confirming what was appreciated by angiography.

EAE Assay: Method and Results

Experimental autoimmune encephalomyelitis (EAE) is possibly the best animal model to study demyelinating diseases of the central nervous system (CNS) such as multiple sclerosis (MS) Since the first classical studies EAE has been an invaluable tool for dissecting mechanisms of the immune response against self-antigens within the CNS, as well as to test new therapies for the treatment of autoimmune diseases. Rodents are susceptible to EAE. Depending upon species, antigens and mode of sensitisation, EAE can have a monophasic acute course or a chronic relapsing, and even a primarily progressive course that mimics human MS. Acute models of EAE allow faster experimentation and observation, whereas chronic models allow wider observation, such as preventive versus therapeutic treatments.

Seven week-old C57 black/6N female mice were immunized with an emulsion of mycobacterium tubercolosis and the peptide spanning the sequence 35aa-55aa of the myelin oligodendrocyte glycoprotein (MOG) dissolved in phosphate buffer and Freud adjuvant. Mice were injected subcutaneously, in three different sites, with a total of 0.3 ml of emulsion. Immediately after the immunization mice were injected intravenously with 0.1 ml of pertussin toxin (500 ng/µl). After hours from the immunization mice received a second challenge with pertussin toxin. This model has been previously described (Furlan, R.; Brambilla, E.; Sanvito, F.; Roccatagliata, L.; Olivieri, S.; Bergami, A.; Pluchino, S.; Uccelli, A.; Comi, G.; Martino, G. Vaccination with amyloid-beta peptide induces autoimmune encephalomyelitis in C57/BL6 mice. Brain, 2003, 126, 285-291) and characterised by onset at day 10-12, rapid progression in. 3-4 days and a stabilisation period during which the clinical score remain stable.

After 4 days from the immunization a group of mice were injected intraperitoneally with 5 mg/kg of the compound of. 1-(3-chlorophenyl)-3-phenyl-pyrrole-2,5-dione of Example. 63 every day.

Starting from day 10 after the immunization mice were evaluated daily for weight loss and locomotive defects.

A non parametric scale was used to evaluate clinical signs of EAE. Scores were assigned according the following parameters: 0=healthy, 1=weak or flaccid tail, 2=unsteady gait (ataxia), hind limb paresis, or slow righting reflex, 3=paraparesis, complete hind paralysis, 4=paraparesis with fore limb involvement, 5=moribund or death.

Figure 2:
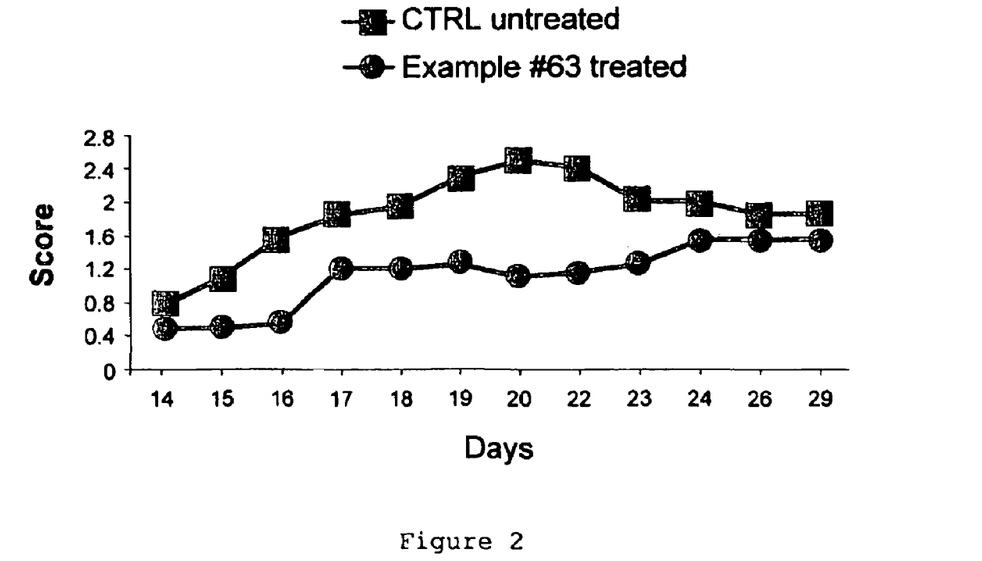
FIG. 2 shows the average score of the non parametric test obtained from the observation of two groups of mice.

The average score of the non parametric test obtained from the observation of the two groups of mice is reported beloia. Treatment with 1-(3-chlorophenyl)-3-phenyl-pyrrole-2,5-dione of Example 63 significantly prevented the development of the disease. Strikingly while approximately 30% of the mice subjected to EAE developed inferior art Paresis after 20 days, no one of the mice treated with the compound showed similar signs of disease (FIG. 2).

The invention claimed is:

1. A method of treating diabetic retinopathy, comprising administering, to a subject in need thereof, a therapeutically effective amount of at least one compound selected from the group consisting of:
   1-(3-chlorophenyl)-3-(4-fluorophenyl)-pyrrole-2,5-dione;
   1-(3-chlorophenyl)-3-(3-fluorophenyl)-pyrrole-2,5-dione;
   1-(3-chloro-4-fluorophenyl)-3-(3-fluorophenyl)-pyrrole-2,5-dione;
   1-(3-chlorophenyl)-3-(2-fluorophenyl)-pyrrole-2,5-dione;

1-(3-chloro-4-fluorophenyl)-3-(2-fluorophenyl)-pyrrole-2,5-dione;
1-(3-bromophenyl)-3-phenyl-pyrrole-2,5-dione;
1-(3-methylphenyl)-3-phenyl-pyrrole-2,5-dione;
1-(3-trifluoromethylphenyl)-3-phenyl-pyrrole-2,5-dione;
1-(3-chlorophenyl)-3-(4-hydroxyphenyl)-pyrrole-2,5-dione;
1-(3-chlorophenyl)-3-(4-methoxyphenyl)-pyrrole-2,5-dione;
1-(3-methylphenyl)-3-(4-chlorophenyl)-pyrrole-2,5-dione;
1-(3-chlorophenyl)-3-(4-chlorophenyl)-pyrrole-2,5-dione;
1-(3-chlorophenyl)-3-(4-methylphenyl)-pyrrole-2,5-dione;
1-(5-chloro-2-methoxyphenyl)-3-phenyl-pyrrole-2,5-dione;
1-(3-chloro-4-fluorophenyl)-3-phenyl-pyrrole-2,5-dione; and
1-(3-chlorophenyl)-3-phenyl-pyrrole-2,5-dione.

2. A method according to claim 1, comprising administering a therapeutically effective amount of 1-(3-chlorophenyl)-3-(4-fluorophenyl)-pyrrole-2,5-dione.

3. A method according to claim 1, comprising administering a therapeutically effective amount of 1-(3-chlorophenyl)-3-(3-fluorophenyl)-pyrrole-2,5-dione.

4. A method according to claim 1, comprising administering a therapeutically effective amount of 1-(3-chloro-4-fluorophenyl)-3-(3-fluorophenyl)-pyrrole-2,5-dione.

5. A method according to claim 1, comprising administering a therapeutically effective amount of 1-(3-chlorophenyl)-3-(2-fluorophenyl)-pyrrole-2,5-dione.

6. A method according to claim 1, comprising administering a therapeutically effective amount of 1-(3-chloro-4-fluorophenyl)-3-(2-fluorophenyl)-pyrrole-2,5-dione.

7. A method according to claim 1, comprising administering a therapeutically effective amount of 1-(3-bromophenyl)-3-phenyl-pyrrole-2,5-dione.

8. A method according to claim 1, comprising administering a therapeutically effective amount of 1-(3-methylphenyl)-3-phenyl-pyrrole-2,5-dione.

9. A method according to claim 1, comprising administering a therapeutically effective amount of 1-(3-trifluoromethylphenyl)-3-phenyl-pyrrole-2,5-dione.

10. A method according to claim 1, comprising administering a therapeutically effective amount of 1-(3-chlorophenyl)-3-(4-hydroxyphenyl)-pyrrole-2,5-dione.

11. A method according to claim 1, comprising administering a therapeutically effective amount of 1-(3-chlorophenyl)-3-(4-methoxyphenyl)-pyrrole-2,5-dione.

12. A method according to claim 1, comprising administering a therapeutically effective amount of 1-(3-methylphenyl)-3-(4-chlorophenyl)-pyrrole-2,5-dione.

13. A method according to claim 1, comprising administering a therapeutically effective amount of 1-(3-chlorophenyl)-3-(4-chlorophenyl)-pyrrole-2,5-dione.

14. A method according to claim 1, comprising administering a therapeutically effective amount of 1-(3-chlorophenyl)-3-(4-methylphenyl)-pyrrole-2,5-dione.

15. A method according to claim 1, comprising administering a therapeutically effective amount of 1-(5-chloro-2-methoxyphenyl)-3-phenyl-pyrrole-2,5-dione.

16. A method according to claim 1, comprising administering a therapeutically effective amount of 1-(3-chloro-4-fluorophenyl)-3-phenyl-pyrrole-2,5-dione.

17. A method according to claim 1, comprising administering a therapeutically effective amount of 1-(3-chlorophenyl)-3-phenyl-pyrrole-2,5-dione.

* * * * *